United States Patent
Grabstein et al.

(10) Patent No.: US 10,214,761 B2
(45) Date of Patent: Feb. 26, 2019

(54) AMINO ACID DERIVATIVES

(71) Applicant: MEDIMMUNE LIMITED, Cambridge (GB)

(72) Inventors: Kenneth H. Grabstein, Mercer Island, WA (US); Michael Van Brunt, Covington, WA (US); Marcello Marelli, Seattle, WA (US)

(73) Assignee: MEDIMMUNE LIMITED, Cambridge, MA (US)

( * ) Notice: Subject to any disclaimer, the term of this patent is extended or adjusted under 35 U.S.C. 154(b) by 0 days.

(21) Appl. No.: 15/610,931

(22) Filed: Jun. 1, 2017

(65) Prior Publication Data

US 2017/0306380 A1 Oct. 26, 2017

Related U.S. Application Data

(62) Division of application No. 14/430,412, filed as application No. PCT/EP2013/069888 on Sep. 24, 2013, now Pat. No. 9,670,521.

(60) Provisional application No. 61/862,495, filed on Aug. 5, 2013, provisional application No. 61/705,116, filed on Sep. 24, 2012.

(51) Int. Cl.
| | | |
|---|---|---|
| *C12P 21/02* | (2006.01) | |
| *A61K 47/68* | (2017.01) | |
| *C07C 271/12* | (2006.01) | |
| *C07C 271/20* | (2006.01) | |
| *C07C 271/22* | (2006.01) | |
| *C07C 233/49* | (2006.01) | |
| *C07C 233/56* | (2006.01) | |
| *C07C 247/04* | (2006.01) | |
| *C07C 235/74* | (2006.01) | |
| *C07K 16/24* | (2006.01) | |
| *C07K 16/32* | (2006.01) | |
| *C07K 16/46* | (2006.01) | |
| *C07K 17/08* | (2006.01) | |
| *C07K 14/435* | (2006.01) | |
| *C07K 16/28* | (2006.01) | |
| *C07K 16/40* | (2006.01) | |
| *C12N 9/00* | (2006.01) | |
| *C12N 15/85* | (2006.01) | |

(52) U.S. Cl.
CPC .......... *C12P 21/02* (2013.01); *A61K 47/6851* (2017.08); *C07C 233/49* (2013.01); *C07C 233/56* (2013.01); *C07C 235/74* (2013.01); *C07C 247/04* (2013.01); *C07C 271/12* (2013.01); *C07C 271/20* (2013.01); *C07C 271/22* (2013.01); *C07K 14/43595* (2013.01); *C07K 16/244* (2013.01); *C07K 16/248* (2013.01); *C07K 16/2863* (2013.01); *C07K 16/32* (2013.01); *C07K 16/40* (2013.01); *C07K 16/46* (2013.01); *C07K 17/08* (2013.01); *C12N 9/93* (2013.01); *C12N 15/85* (2013.01); *C07K 2317/14* (2013.01); *C07K 2317/24* (2013.01); *C07K 2317/31* (2013.01); *C07K 2317/40* (2013.01); *C07K 2317/51* (2013.01); *C12Y 301/01025* (2013.01); *C12Y 601/01* (2013.01); *C12Y 601/01025* (2013.01)

(58) Field of Classification Search
CPC ... C07C 233/49; C07C 233/56; C07C 235/74; C07C 247/04; C07C 271/12; C07C 271/20; C07C 271/22; C07K 14/43595; C07K 16/244; C07K 16/248; C07K 16/2863; C07K 16/32; C07K 16/40; C07K 16/46; C07K 17/08; C07K 2317/14; C07K 2317/24; C07K 2317/31; C07K 2317/40; C07K 2317/51; C12N 15/85; C12N 9/93; C12P 21/02; C12Y 301/01025; C12Y 601/01; C12Y 601/01025
See application file for complete search history.

(56) References Cited

U.S. PATENT DOCUMENTS

| | | | |
|---|---|---|---|
| 3,711,458 A | 1/1973 | Olofson | |
| 4,512,979 A | 4/1985 | Patchett | |
| 5,216,023 A | 6/1993 | Nagy | |
| 8,168,407 B2 | 5/2012 | Yokoyama et al. | |
| 9,732,367 B2 | 8/2017 | Grabstein et al. | |
| 2004/0146941 A1* | 7/2004 | Zhang | C07C 217/28 506/31 |
| 2010/0304431 A1 | 12/2010 | Yokoyama et al. | |
| 2016/0024522 A1 | 1/2016 | Dieci et al. | |
| 2017/0306381 A1 | 10/2017 | Grabstein et al. | |

FOREIGN PATENT DOCUMENTS

| | | |
|---|---|---|
| EP | 1911840 A1 | 4/2008 |
| GB | 2470770 A | 8/2010 |
| WO | 2004041752 A2 | 5/2004 |
| WO | 2011044255 A1 | 4/2011 |

(Continued)

OTHER PUBLICATIONS

Dose et al., "Single nucleotide specific detection of DNA by native chemical ligation of fluorescence labeled PNA-probes," Bioorganic and Medicinal Chemistry 16 (2008) 65-77.*
Isidro-Llobet et al, "Amino Acid-Protecting Groups," Chem. Rev. 2009, 109, 2455-2504.*
Coward et al, "Analogs of 5-adenosylhomocysteine as potential inhibitors of biological transmethylation. Synthesis and biological activity of homocysteine derivatives bridged to adenine", J. Med. Chem., 15(4), 381-384 (1972).

(Continued)

*Primary Examiner* — Pancham Bakshi
*Assistant Examiner* — Mark R Luderer
(74) *Attorney, Agent, or Firm* — Medler Ferro Woodhouse & Mills, PLLC

(57) ABSTRACT

There are provided amino acid derivatives of formula V and VI as defined herein which are pyrrolysine analogs for use in bioconjugation processes.

16 Claims, 2 Drawing Sheets

Specification includes a Sequence Listing.

(56) References Cited

FOREIGN PATENT DOCUMENTS

| WO | WO2011044255 | * | 4/2011 |
|---|---|---|---|
| WO | 2011087810 A1 | | 7/2011 |
| WO | WO2011/087808 | * | 7/2011 |
| WO | 2012032181 A1 | | 3/2012 |
| WO | 2012038706 A1 | | 3/2012 |
| WO | 2012/104422 | | 8/2012 |
| WO | 2014/036492 A1 | | 3/2014 |

OTHER PUBLICATIONS

Erickson et al, "Use of chlorinated benzyloxycarbonyl protecting groups to eliminate N. epsilon-branching at lysine during solid-phase peptide synthesis", J.A.C.S., 95(11), 3757-3763 (1973).

Jermyn "Carbobenzoxy derivatives of S-aminoalkyl-L-cysteines", Australian Journal of Chemistry, 19(10), 1999-2000 (1966).

Jie Li et al: "Ligand-free palladium-mediated site-specific protein labelling inside gram-negative bacterial pathogens", J.A.C.S., 135(19), 7330-7338, (2013).

Kimbonguila et al, "Allylic protection of thiols and cysteine: I: The allyloxycarbonylaminomethyl group", Tetrahedron, 55(22), 6931-6944 (1999).

Ledger et al, "The use of sequestering agents in the preparation of [epsilon]acyl-L-lysine and [delta]acyl-L-ornithine derivatives", Australian Journal of Chemistry, 18(6), 933-935, (1965).

Lindley "The preparation of compounds related to S-2-aminoethyl-L-cysteine" Australian Journal of Chemistry 12(2), 296-298, (1959).

Matsui, "Studies on acylase activity and microorganisms. XXIV. Properties of [delta]-ornithine acylase: 5-N-acylomithine amidohydrolase", Chem. Pharm. Bull., 15(10), 1586-1596 (1967).

Nishino et al, "Tandem enzymatic relsolution yielding L-alpha-aminoalkanedioic acid omega-esters", Chem. Pharm. Bull., 44(1), 212-214 (1996).

Noda et al, "Modified benzyloxycarbonyl groups for protection of [epsilon]-amino group of lysine", Bull. Chem. Soc. Japan, 43(6), 1883-1885 (1970).

Plass et al, "Genetically encoded copper-free click chemistry", Angewandte Chemie, Int Edition, 50(17), 3878-3881 (2011).

Popovitz-Biro et al, "A new series of amphiphilic molecules forming stable Z-type (polar) Langmuir-Blodgett films", 112(7), 2498-2506 (1990).

Spanton et al, "Chemical defence and self-defence: Biochemical transformations of contact insecticides produced by soldier termites", Tetrahedron, 38(13), 1921-1930 (1982).

Theodoropoulos, "Synthesis of [epsilon]-peptides of lysine", J. Org. Chem. 23(1), 140, (1958).

Xin Li et al, "N6-(2-(R)-propargylglycyl)lysine as a clickable pyrrolysine mimic", Chemistry—An Asian Journal, 5(8), 1765-1769 (2010).

Zhang et al, "Mechanism of inactivation of neuronal nitric oxide synthase by N[omega]-allyl-L-arginine", J.A.C.S., 119(45), 10888-10902 (1997).

Sun et al., "Vitamin K epoxide reductase significantly improves carboxylation in a cell line overexpressing factor X", Blood, 106(12):3811-3813 (2005).

International Search Report dated Nov. 14, 2013, in PCT/EP2013/069887 (5 pages).

International Search Report dated Jan. 3, 2014, in PCT/EP2013/069888 (4 pages).

International Search Report dated Jul. 4, 2015, in PCT/IB2014/002505 (8 pages).

Axup et al., "Synthesis of site-specific antibody-drug conjugates using unnatural amino acids", P.N.A.S. 109(40), (2012) 16101-16106.

Dose et al., "Single nucleotide specific detection of DNA by native chemical ligation of fluorescence labelled PNA-probes", Bioorg. Med. Chem., 16, (2008) 65-77.

Hancock et al., "Expanding the Genetic Code of Yeast for Incorporation of Diverse Unnatural Amino Acids via a Pyrrolysyl-tRNA Synthetase/tRNA Pair", J. Am. Chem. Soc., 132, (2010), 14819-14824.

Mukai et al., "Addling L-lysine derivatives to the genetic code of mammalian cells with engineered pyrrolysyl-tRNA synthetases", Biochemical and Biophysical Research Communications, 371 (2008), 818-822.

Vrabel et al., "Optimization of the posttranslational click modification of proteins", Collect. Czech. Chern. Commun. 76(9), (2011) 1089-1101.

Yasobu et al., "Design, Synthesis and Antitumor Activity of 4-Halocolchicines and their Pro-drugs Activated by Cathepsin B", ACS Med. Chem. Lett., 2, (2011) 348-352.

* cited by examiner

AMINO ACID DERIVATIVES

CROSS-REFERENCE TO RELATED APPLICATIONS

This application is a divisional of U.S. patent application Ser. No. 14/430,412, filed Mar. 23, 2015, now U.S. Pat. No. 9,670,521, which is the U.S. national phase application of International Patent Application No. PCT/EP2013/069888, filed Sep. 24, 2013, which claims priority to U.S. Provisional Application Nos. 61/705,116, filed Sep. 24, 2012 and 61/862,495, filed Aug. 5, 2013, the entire disclosures of each of which are incorporated by reference herein in their entirety.

The invention relates to amino acid derivatives for use in bioconjugation processes.

REFERENCE TO SEQUENCE LISTING SUBMITTED ELECTRONICALLY

The content of the electronically submitted sequence listing in ASCII text file entitled 304_0038USD1_SeqListing.txt and having a size of 38 kilobytes filed with the application is incorporated herein by reference in its entirety.

INTRODUCTION

Pyrrolysine is a natural amino acid, the only one that is authentically specified by an amber codon. It uses a 21st aminoacyl-tRNA synthetase (PylRS), naturally evolved to be orthogonal to all other amino acids and tRNAs. Blight et Al., 2004 showed that PylRS and its counterpart tRNA (tRNApyl) can incorporate pyrrolysine at amber codons in E. coli. They also showed that the wt PylRS is naturally promiscuous and can incorporate analogs of lysine.

Yokoyama et al (EP1911840) demonstrated that the PylRS/tRNApyl system is orthogonal in eukaryotic cells and showed the incorporation of several non natural amino acids (nnAAs) into a target proteins encoded by amber codons in bacterial cells. These authors also identified key amino acid residues in pylRS that form the amino acid binding pocket and function in selecting pyrrolysine over other canonical amino acids. Mutations at this site generated mutants able the recognize and aminoacylate the tRNApyl with AzZ-lys (Yanagisawa 2008).

This orthogonality extends to bacteria and eukaryotic cells.

PylRS is a naturally promiscuous synthetase that has naturally evolved to exclude lysine, but will incorporate lysine analogs without mutation, including azides, alkynes and alkenes, (Yanagisawa et al, 2008; Neumann et al. 2008; Mukai et al., 2008; Nguyen et al., 2009). The basis of this specificity is dependent on hydrophobic interactions between amino acid residues of the pylRS binding pocket with the pyrrole ring of pyrrolysine that stabilizes and correctly positions the amino acid in the active site of the synthetase (Kavran et al., 2007). This RS/tRNA pair has been introduced via transient transfection into bacterial, yeast and mammalian cells and shown to be effective for incorporation of a number of non-natural amino acids into target proteins.

For instance, EP 1911840 demonstrates incorporation of N-ε-boc-Lysine into a target protein in E. coli cells.

Pyrrolysine analogs, defined as amino acid derivatives recognized by either native or genetically evolved PylRS and incorporated into proteins at amber codon sites, have been disclosed in the past few years and reviewed, for instance, by Feckner et. al (Fekner, Li, & Chan, 2010) and Liu et al. Analogs bearing functional groups or post translational modifications have been site-specifically incorporated into proteins using pylRS-tRNApyl systems. Several studies, see e.g. Yanagisawa et al , focused on mutations within the PylRS enzyme in order to accommodate analogs in which the N6 substituent were an aromatic ring within the binding pocket pyrrolysine. Others, for instance Nguyen et al (also in WO2010/139948) , and Li et al (also in WO2011/044255) focused on identification of pyrrolysine analogs which do not carry a bulky N6 substituent, with the result of obtaining simpler analogs which would be simple to synthesize and interact with native pylRS/tRNApyl pairs. Furthermore, Chin et al developed two analogs with terminal alkyne and azide groups, amenable to use for protein labeling via copper catalyzed click chemistry (CUAAC).

There remains a need to develop further pyrrolysine analogs. Whilst pyrrolysine analogs made thus far have been restricted to those evolved from a lysine backbone, the present inventors have generated pyrrolysine analogs successfully incorporated into proteins with native pylRS/tRNApyl pairs starting from a variety of amino acid structures.

SUMMARY OF THE INVENTION

According to the invention there are provided pyrrolysine analogues of formulae V and VII as described herein.

There is also provided a mutant protein containing as non-natural amino acid one or more (e.g. one) pyrrolysine analogues of formulae V and VII as described herein.

There is also provided an antibody containing as non-natural amino acid one or more (e.g. one) pyrrolysine analogues of formulae V and VII as described herein in each heavy and/or light chain.

There is also provided a mutant protein or antibody as aforesaid which is conjugated via the one or more (e.g. one) non-natural amino acids to one or more (e.g. one) moieties selected from proteins, cytotoxic agents, drugs and polymers.

There is also provided use of a pyrrolysine analogue as aforesaid in the manufacture of a mutant protein e.g. antibody containing one or more non-natural amino acids.

Amino acid analogs described in the present invention are new and useful and have the merit of being straightforward to prepare, in being readily incorporated into proteins (typically without loss of bioactivity when used appropriately) and in providing useful means for bioconjugation.

BRIEF DESCRIPTION OF THE SEQUENCES OF THE SEQUENCE LISTING

Figure 1:
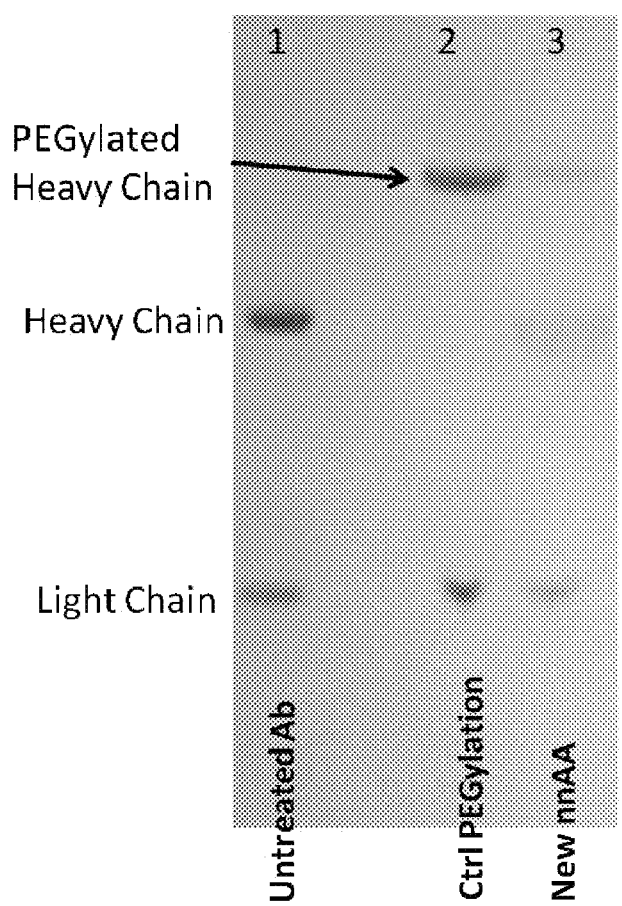
FIG. 1. PEGylation of azide containing monoclonal antibodies. Lane 1: Untreated Antibody, Lane 2: Antibody with pyrrolysine analog Formula V.1 incorporated into heavy chain and subjected to PEGylation conditions; Lane 3: Antibody with pyrrolysine analog Formula VI.1 incorporated into heavy chain and subjected to PEGylation conditions.

SEQ ID No 1: PylRS *Methanosarcina mazei* WT nucleotide sequence

SEQ ID No 2: PylRS *Methanosarcina mazei* WT amino acid sequence

SEQ ID No 3: PylRS *Methanosarcina mazei*, Y384F Mutant nucleotide sequence

SEQ ID No 4: PylRS *Methanosarcina mazei*, Y384F Mutant amino acid sequence

SEQ ID No 5: tRNApyl *Methanosarcina mazei*

SEQ ID No 6: U6 snRNA Promoter

SEQ ID No 7: U6-tRNApyl construct

SEQ ID No 8: GFP nucleotide sequence

SEQ ID No 9: GFP amino acid sequence

SEQ ID No 10: GFPY40 nucleotide sequence

SEQ ID No 11: GFPY40 amino acid sequence

SEQ ID No 12: anti-Her2 (4D5) gamma nucleotide sequence

SEQ ID No 13: anti-Her2 (41)5) gamma amino acid sequence

SEQ ID No 14: anti-Her2 (4D5) gamma_K274amber nucleotide sequence

SEQ ID No 15: anti-Her2 (4D5) gamma_K274amber amino acid sequence

SEQ ID No 16: anti-Her2 (4D5) Kappa nucleotide sequence

SEQ ID No 17: anti-Her2 (4D5) Kappa amino d sequence

DETAILED DESCRIPTION OF THE INVENTION

Definitions

The term "amide" refers to a —C(=O)—NH— linkage.

The term "carbamate" refers to a —O—C(=O)—NH— linkage.

The term "ester" refers to a —C—C(=O)—O—C linkage

The term "alkyl" refers to an aliphatic linkage or substituent, typically containing 1-6 e.g. 1-4 carbon atoms and can be straight chain or branched. Examples include methyl, ethyl, n-propyl, i-propyl, n-butyl and t-butyl.

The term "alkoxy" refers to the group —O-alkyl.

The term "alkenyl", "alkene" or "olefin" refers to an aliphatic linkage or substituent, typically containing 2-6 e.g. 2-4 carbon atoms and can be straight chain or branched and which is unsaturated in respect of containing at least one C=C moiety. Examples include ethenyl, propen-1-yl, propen-2-yl, and 2-methyl-propen-2-yl. An alkenyl group may be optionally substituted e.g. by one or more (e.g. 1) substituents such as halogen (e.g. Cl) or an ether group (e.g. —O—$C_{1-6}$alkyl) although suitably it is not substituted.

The term "alkynyl" or "alkyne" refers to an aliphatic linkage or substituent, typically containing 2-6 e.g. 2-4 carbon atoms and can be straight chain or branched and which is unsaturated in respect of containing at least one C≡C moiety. Examples include —C≡CH and —C≡C—$CH_3$. An alkynyl group may be optionally substituted e.g. by one or more (e.g. 1) substituents such as halogen (e.g. Cl) or an ether group (e.g. —O—$C_{1-6}$alkyl) although suitably it is not substituted.

The term "cycloalkyl" refers to an alicyclic and unsaturated compound typically containing 3 to 8 cyclic carbon atoms. Cycloalkyl groups may containing branching. The total number of carbon atoms will typically be 3 to 10. Exemplary groups include cyclopropyl, cyclobutyl, cyclopentyl, 3-methyl-cyclopropyl and cyclohexyl.

The term "cycloalkenyl" refers to an alicyclic compound typically containing 5 to 8 cyclic carbon atoms and containing at last one C=C moiety. Cycloalkenyl groups may containing branching. The total number of carbon atoms will typically be 5 to 10. Exemplary groups include cyclopentenyl, 3-methyl-cyclopropenyl and cyclohexenyl.

The term "heterocyclyl" refers to a cycloalkyl or cycloalkenyl moiety in which the ring contains one or more (e.g. one, two or three, such as one or two, especially one) heteroatom selected from O, N and S. Examples include azetidine, pyrrolidine, piperidine, piperazine, N-methylpiperazine, morpholine and thiomorpholine.

The term "aryl" refers to an aromatic ring structure that can be part of a linkage or part of a substituent. Aryl moieties may contain one ring (e.g. phenyl) or two rings (e.g. naphthyl). Aryl groups may be substituted e.g. by one or more (e.g. one or two, such as one) substituent selected from alkyl, alkenyl, alkynyl, fluoroalkyl, halogen, alkoxy, nitro and cyano. An exemplary aryl is phenyl.

The term "heteroaryl" refers to a heteroaromatic ring structure that can be part of a linkage or part of a substituent. The heteroaromatic ring may contain 1-4 (more usually 1-3 e.g. one or two) heteroatoms selected from O, N and S. Heteroaryl moieties may contain one ring or two rings. Example groups containing one 6 membered ring include pyridine and pyrimidine. Example groups containing one 5 membered ring include pyrrole, furan, thiophene, oxazole, thiazole, diazole, thiadiazole and tetrazole. Heteroaryl moieties that contain two rings may contain heteroatoms in one or both rings. Examples include quinoline and isoquinoline. Heteroaryl groups may be substituted e.g. by one or more (e.g. one or two, such as one) substituent selected from alkyl, alkenyl, alkynyl, fluoroalkyl, halogen, alkoxy, nitro and cyano.

The term "aromatic halide" refers to an aromatic ring (typically phenyl) which is substituted by at least one (e.g. one) halo group such as fluorine, chloride, bromide or iodine. Said aromatic ring may contain further substituents e.g. those mentioned for aryl.

The term "azide" and "azido" refers to a N=N(+)=N(-) functional group.

The term "cycloalkyne" refers to a cyclic arrangement of carbon atoms (typically 6-9 membered, especially 8-9 membered) which includes a carbon-carbon triple bond captured in the ring structure. Examples include cyclooctyne and cyclononyne. A further example is benzyne. Cycloalkyne groups may containing branching. The total number of carbon atoms will typically be 6 to 12 e.g. 6 to 10.

The term "ketone" refers to a C—C(=O)—C linkage.

The term "pyrrolysine analog" means an amino acid derivative recognized by either native or genetically evolved PylRS and incorporated into proteins at an amber codon site.

The expression "the side chain of one of the 20 natural amino acids" refers to the group R in the formula HOOC—CHR—$NH_2$ relating to the 20 natural amino acids known by their single letter codes A, C, D, E, F, G, H, I, K, L, M, N, P, Q, R, S, T, V, W and Y. Either L or S stereochemistry (or a mixture thereof) is intended, although L stereochemistry is preferred.

The present invention discloses pyrrolysine analogs.

Some pyrrolysine analogs of the present invention have the structure of Formula V:

Formula V $$HO_2C-\underset{H_2N}{\overset{H}{\underset{|}{C}}}-\left(\underset{H}{\overset{H}{\underset{|}{C}}}\right)_4-\underset{H}{\overset{O}{\underset{}{N}}}-\overset{O}{\underset{}{C}}-Z-\left(\underset{H}{\overset{H}{\underset{|}{C}}}\right)_b-FG$$

wherein

Z=bond, CH$_2$, CH—NH$_2$, CH—OH, NH, O, S or CH—NH$_2$;

b is 0 or an integer 1-7; and

FG=azide, alkene, alkyne, ketone, ester, aryl or cycloalkyne.

In formulae V when FG represents aryl, an example is aromatic halide e.g. 4-halo phenyl such as 4-iodo phenyl.

Moiety Z(CH$_2$)$_b$FG may, for example, represent CO-aryl e.g. CO-phenyl or —COalkyl e.g. —COMe. Exemplary compounds of formula V are the following:

Formula V.1

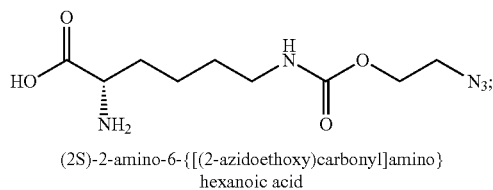

(2S)-2-amino-6-{[(2-azidoethoxy)carbonyl]amino}hexanoic acid

Formula V.2

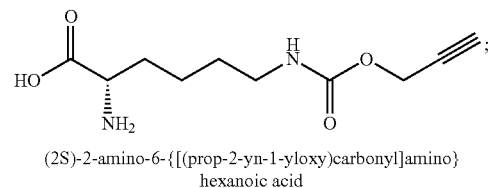

(2S)-2-amino-6-{[(prop-2-yn-1-yloxy)carbonyl]amino}hexanoic acid

Formula V.3

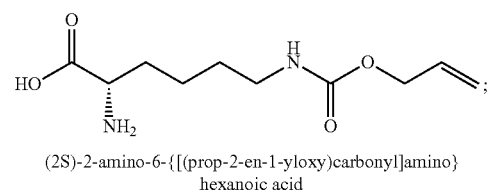

(2S)-2-amino-6-{[(prop-2-en-1-yloxy)carbonyl]amino}hexanoic acid

Formula V.4

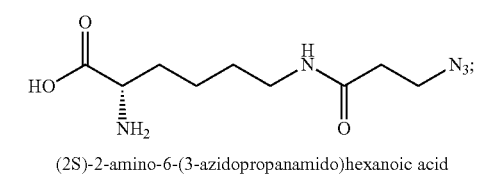

(2S)-2-amino-6-(3-azidopropanamido)hexanoic acid

Formula V.5

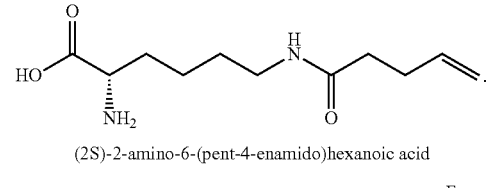

(2S)-2-amino-6-(pent-4-enamido)hexanoic acid

Formula V.6

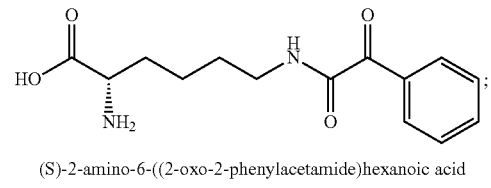

(S)-2-amino-6-((2-oxo-2-phenylacetamide)hexanoic acid

Formula V.7

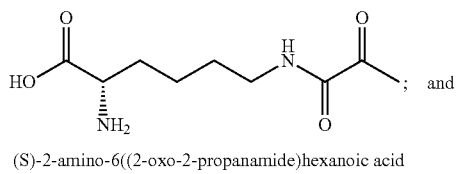

; and (S)-2-amino-6((2-oxo-2-propanamide)hexanoic acid

Formula V.8

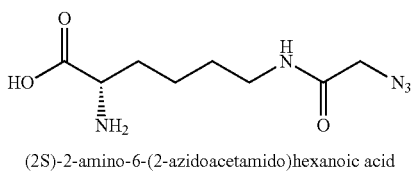

(2S)-2-amino-6-(2-azidoacetamido)hexanoic acid

Alternative pyrrolysine analogs suitable for use as non natural amino acids in the present invention have the structure of Formula VI:

Formula VI

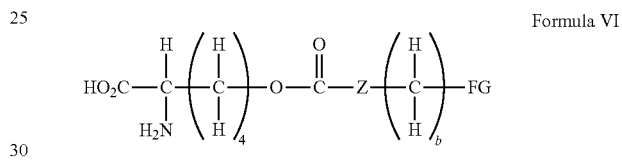

wherein

Z=CH$_2$, CH—NH$_2$, CH—OH, NH, O or S;

FG=azide, alkene, alkyne, ketone, ester, aryl or cycloalkyne; and b=an integer 1-4.

In formulae VI when FG represents aryl, an example is aromatic halide e.g. 4-halo phenyl such as 4-iodo phenyl.

Suitbly Z represents NH. In another embodiment it represents CH.

b may, for example, represent 1 or 2.

FG may, for example, represent —N$_3$, —CH=CH$_2$, —C≡CH, —COCH$_3$, COOCH$_3$, phenyl substituted by halogen or cyclooctyne.

Exemplary compounds of Formula VI are:

Formula VI.1

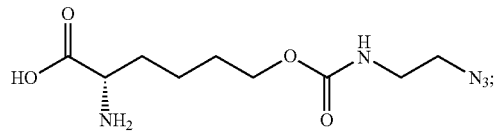

(2S)-2-amino-6-{[(2-azidoethyl)carbamoyl]oxy}hexanoic acid

Formula VI.2

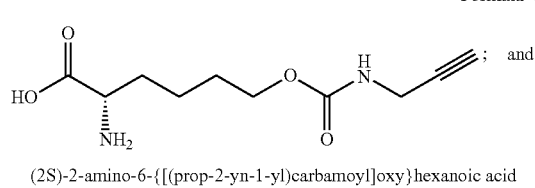

; and (2S)-2-amino-6-{[(prop-2-yn-1-yl)carbamoyl]oxy}hexanoic acid

Formula VI.3

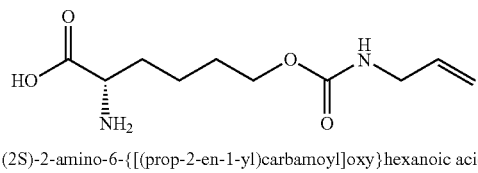

(2S)-2-amino-6-{[(prop-2-en-1-yl)carbamoyl]oxy}hexanoic acid

In structures of formulae V and VI, when FG represents alkene, it suitably represents —CH═CH$_2$ or —CH═CH—CH$_3$, preferably —CH═CH$_2$.

In structures of formulae V and VI, when FG represents alkyne, it suitably represents —C≡CH or —C≡C—CH$_3$, preferably —C≡CH.

In structures of formulae V and VI, when FG represents ketone, it suitably represents —C(═O)—CH$_3$ or —C(═O)—CH$_2$—CH$_3$, preferably —C(═O)—CH$_3$.

In structures of formula VI, when FG represents ketone it may, for example, represent —C(═O)-aryl e.g. —C(═O)-phenyl.

In structures of formulae V and VI, when FG represents ester, it suitably represents —C(═O)—Oalkyl e.g. —C(═O)—Omethyl.

In structures of formulae V and VI, when FG represents aromatic halide, it suitably represents phenyl substituted by halogen, especially iodine (e.g. 4-iodo-phenyl).

In structures of formulae V and VI, when FG represents cycloalkyne, it suitably represents cyclooctyne, e.g. cyclooct-4,5-yne.

Advantageously, the nnAAs of formulas V and VI of the present invention have been shown to have good incorporation as demonstrated by GFP assay. Formula VI.1 had a similar level of translational compentency to Formula V.1 in the GFP assay incorporation assay. Both the Formula V and VI are easily modified to incorporate a variety of useful functional groups which can be used for site selective post translational modification. Alkynes and alkenes are readily incorporated. The pyrrolysine analogs disclosed herein can be made using various methods. The reaction conditions can generally be determined by one of the ordinary skill in the art.

Formula V analogs are readily prepared by the addition of an activated carbonyl group, such as a chloroformate, activated carboxylic acid ester, isocyanate, activated carbonate or sulfonyl halide to a mono-protected diamino substrate of type 1, in which the a-amino group is protected by a protecting group ("PG") such as a Boc, Cbz, TFA, Acetyl or Fmoc group (see Scheme 1). The coupled product 3 can undergo further modifications, such as the displacement of halides with an azido nucleophile to install the desired functionality. Otherwise, the intermediate 3 is deprotected to remove the a-amino acid masking group to afford the desired Formula V analog.

Scheme 1:

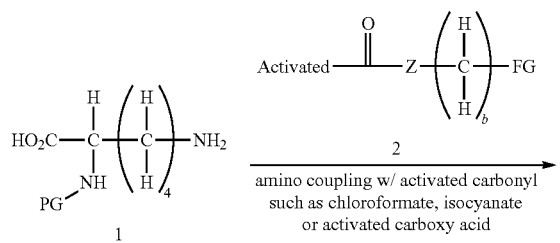

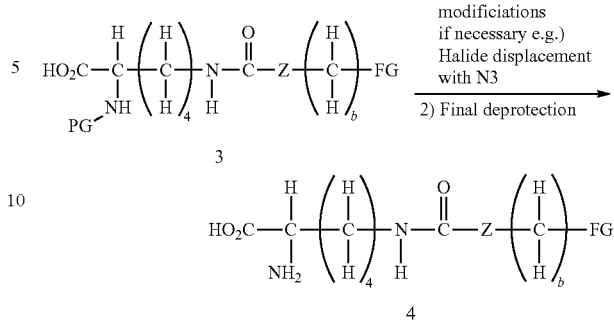

Formula VI analogs were prepared by conjugation of hydroxyl amino acids 9 to substrates with activated carbonyls such as carboxylic acid ester, isocyanate, acid chlorides, activated carbonates or sulfonyl halides. The coupled product 11 can undergo further modifications, such as the installation of the azide functional group by displacement of leaving groups such as halides or activated alcohols. The desired amino acid analog 12 is obtained by final deprotection to remove the a-amino acid masking group. Protecting groups may be used as per Scheme 1.

See Scheme 2:

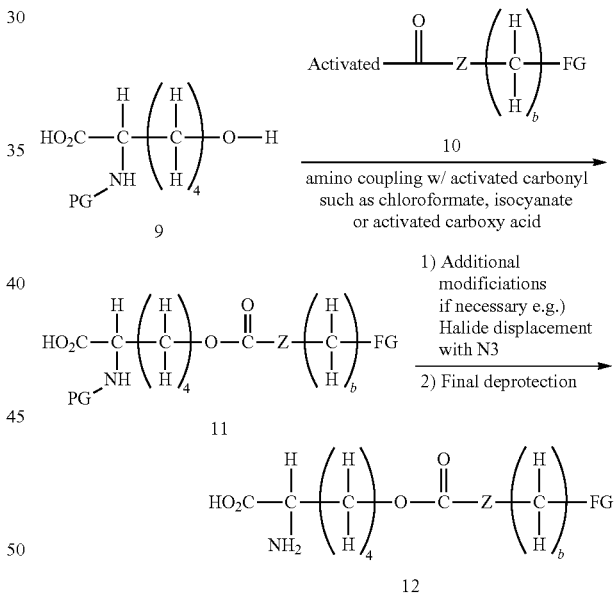

Incorporation of Non-Natural Amino Acid Into Proteins

The pyrrolysine analogs disclosed herein can be incorporated into recombinant proteins. In particular, site specific incorporation of the analog into a recombinant protein can be achieved through amber suppression, wherein a nonsense (amber) codon is inserted within the nucleotide sequence encoding the recombinant protein, at a site where the pyrrolysine analog is to be inserted. The mutated nucleotide sequence, along with one or more plasmids encoding the PylRS and tRNApyl are inserted into a cell of a cell free expression system.

The host cell may be a eukaryotic cell line which is transformed with a vector comprising a DNA construct as aforesaid.

Alternatively, a cell-free expression system is provided, wherein a synthesis reaction lysate obtained from a host cell comprises at least one component required for the synthesis of polypeptides. The synthesis reaction lysate is obtained from bacterial or eukaryotic cells. Preferably, the synthesis reaction lysate is obtained from eukaryotic cells, more preferably, from rabbit reticulocytes or wheat germ.

Preferably, the cell-free expression system is capable of expressing WT PylRS and tRNApyl of the present invention, wherein tRNApyl is introduced into the cells used to obtain the synthesis reaction lysate with DNA constructs of the invention.

Cell-free expression systems suitable for use in the present invention are described for instance in WO201008110, WO2010081111, WO2010083148, incorporated in their entirety herein by reference.

When the pyrrolysine analog is added to the cell or expression system, said analog is incorporated in the recombinant protein at the specified position. The nnAA and the tRNApyl are bound by the pylRS and the tRNApyl is subsequently aminoacylated with the nnAA. This tRNApyl containing an amber anticodon is released into the cytosol where in response to an amber stop codon can interact with the ribosome and the nnAA released to form a peptide bond with the growing polypeptide chain.

Recombinant proteins modified to incorporate a pyrrolysine analog of the invention include all recombinant proteins amenable to site specific post translational modifications, e.g. therapeutic proteins, for instance cytokines, antibodies and antibody derivatives (such as Fab fragments, or single chain antibodies, e.g. single chain variable fragments (scfvs)), peptides, enzymes, fusion proteins, decoy receptors, protein vaccines, protein hormones, e.g. insulin, growth factors, (e.g. human growth hormone, hGH, hGCSF, hFSH, hHCG). Further proteins modifiable with pyrrolysine analogs of the invention include diagnostic labels, imaging reagents.

Suitably, proteins may be modified site specifically to incorporate one or more than one nnAA (pyrrolysine analog) of the invention. For instance, an antibody may incorporate a nnAA of the invention at the heavy chain, or at the light chain, or at both light and heavy chain Site Specific Conjugation of Proteins with Incorporated Non-Natural Amino Acids Proteins having incorporated pyrrolysine analogs of the present invention may be used for the preparation of functionalized protein conjugates. Molecules that may be conjugated to proteins having incorporated non-natural amino acids include (i) other proteins, e.g. antibodies especially monoclonal antibodies; (ii) polymers e.g. PEG groups or other groups that may cause half life extension in the system; (iv) cytotoxic agents e.g. Auristatin F; and (v) drug moieties e.g. doxorubicin and moieties containing radioactive isotopes. Moreover these modified proteins can be conjugated to drugs or nucleotides for targeted delivery of these potent compounds.

More details of certain embodiments are given below in the discussion of antibody drug conjugates.

Pyrrolysine analogs may conveniently contain a unique chemical group permitting conjugation in a targeted fashion without risk of side reaction with other amino acids. For example non-natural anuno acids may contain azide or alkyne groups permitting reaction with a molecule to be conjugated which contains a corresponding alkyne or azide group using the Huisgen 1,3-dipolar cycloaddition reaction.

Preferred conjugation chemistries of the invention include reactions which are orthogonal to the natural twenty amino acids. Such reactions do not interact or cause side reactions with the native 20 amino acids, they are specific to the functional groups associated with the reaction. Suitably the necessary functional groups are incorporated into the target protein via the pyrrolysine analogs of the present invention.

Further, said reactions proceed under conditions which are not destructive to the protein, for instance aqueous solvents, with a pH range which is acceptable to the protein and maintains its solubility, at a temperature which does not lead to deleterious effects upon the protein.

Increasing the stability of the attachment moiety between the protein and the linker can be advantageous. Conventional methods conjugate to the thiol groups of cysteine by reaction with a maleimide forming a thiol ether. The thiol ether can undergo the reverse reaction releasing the linker drug derivative from the antibody. In an embodiment of the invention, the conjugation chemistry employed between an azide and an alkyne results in an aromatic triazole which is significantly more stable, and not as prone to reversibility.

In addition, the product of the reaction, the linkage between protein and payload, ought to be stable, equal to or greater than the stability associated with conventional linkages (amide, thiol ether). Though not an impediment to conjugation, it is often advantageous if the conjugation reactions can be done under native conditions, as this will eliminate an extra refolding processing step.

Preferred chemical conjugations for production of conjugates of the invention include : a 3+2 alkyne-azide cycloaddition, 3+2 dipolar cycloaddition, Husigen 3+2 cycloaddition, Copper promoted azide-alkyne cycloaddition (CuAAC), Ruthenium promoted azide alkyne cycloaddition (RAAC), metal promoted azide alkyne cycloaddition (MAAC), and strain promoted azide alkyne cycloaddition (SPAAC), palladium based couplings including the Heck reaction, Sonogashira reaction Suzuki reaction Stille coupling Hiyama/Denmark reaction olefin metathesis Diels-alder reaction carbonyl condensation with hydrazine, hydrazide, alkoxy amine or hydroxyl amine; strain promoted cycloadditions with nitriles and nitrile oxides; electron promoted cycloaddition; fragment extrusion cycloaddition; alkene cycloaddition followed by a □-elimination reaction.

According to one preferred embodiment, the incorporated amino acid contains an azide or an alkyne group and the process of chemical modification comprises reacting said azide or alkyne group with a reagent comprising an alkyne or azide group. The envisaged reaction is a Huisgen 1,3-dipolar cycloaddition reaction which leads to production of a triazole linkage. The reagent comprising an alkyne or azide group may be a protein (e.g. an antibody) or a cytotoxic agent or a drug or a substance suitable for half life extension (e.g. a PEG group) which carries an alkyne or azide group optionally via a linker.

Optionally,the Huisgen 1,3-dipolar cycloaddition reaction can be performed in the presence of Cu(I) catalysis.

Preferably, copper catalyzed cycloaddition reactions are carried at room temperature, in acqueous solution in presence of cysteine and tris[(1-benzyl-1H-1,2,3-triazol-4-yl)methyl]amine (TBTA). Alternatively, the copper catalyzed cycloaddition reactions are carried out from 4° C. to 50° C. in aqueous solution in the presence of sodium ascorbate and tris(3-hydroxypropyltriazolylmethyl)amine (THPTA). The reactions can also be carried out in mixed aqueous/organic solution with the organic component consisting of DMSO, DMF, methanol, ethanol, t-butanol, trifluoroethanol, propylene glycol, ethylene glycol and hexylene glycol.

In a variant reaction, the incorporated amino acid contains an azide or an alkene group and the process of chemical modification comprises reacting said azide or alkene group with a reagent comprising an alkene or azide group. The reagent comprising an alkene or azide group may be a protein (eg an antibody) or a toxin or a substance suitable for half life extension (eg a PEG group) which carries an alkyne or alkene group optionally via a linker.

The site specific conjugations between the incorporated nnAA and the target payload can be done with fully folded proteins such as antibodies, antibody fragments, and cytokines. Alternatively, the conjugation can be done on denatured proteins in the presence of denaturants such as sodium dodecylsulfate and urea. The copper catalyzed azide alkyne addition can be done in the presence of denaturants and reducing agents such as dithiothreitol and 2-mercaptoethanol.

When more than one nnAA is incorporated into a target protein (e.g. an antibody), the chemical modification may be the same or different. For example if two nnAAs are incorporated, one may be modified to be conjugated to a drug moiety and one may be modified to be conjugated to a PEG moiety.

Conveniently, upon incorporation of more than one nnAA of the invention bearing different but complementary reactive groups, said nnA.As can react with each other to generate an intramolecular In an embodiment, conjugation chemistry of the invention is used for preparing an antibody drug conjugate. The conjugation chemistry may also be used to assemble antibody-protein conjugates, protein protein conjugates such as bispecifics composed of antibody fragments. The conjugation chemistry may also be used to conjugate polymer bond drug conjugates to targeting agents such antibodies and antibody fragments. The conjugation chemistry can also be used to attach polymers such as PEG to proteins to manipulate pharmacokinetic properties.

PEG Moieties

Target proteins may be conjugated to PEG moieties. PEG moieties may be incorporated into antibody drug conjugates. The PEG moiety may typically have a molecular weight ranging between 0.5 kDa and 40 kDa e.g. 5 kDa and 40 kDa. More preferably, the PEG moiety may have a molecular weight of around 20 kDa. In addition, the PEG moieties can have a molecular weight range from 100-2000 Da. PEG moieties may be straight chain or branched. or multi armed The PEG moieties can be functionalized with terminal alkynes, azides, cyanides, cycloalkynes, alkenes, aryl halides. The PEG can be functionalized in such as way as to be monofunctional, homobifunctional, heterobifunctional, and multi-homofunctional.

Antibody Drug Conjugates (ADCs)

Pyrrolysine analogs according to the invention are particularly useful for production of Antibody Drug Conjugates (recombinant antibody covalently bound by a synthetic linker to a given drug, typically a cytotoxic drug, or else a protein or a PEG group) which are homogeneous nature, in which the number of drugs (or other conjugated molecule) per antibody and position of those drugs upon the antibody are explicitly controlled, whereby monoclonal antibodies containing incorporated non-natural amino acids are obtained and site specifically conjugated to a linker carrying a drug moiety (or other conjugated molecule) through orthogonal chemistry.

ADCs obtained with pyrrolysine analogs of the present invention may be manufactured following methods including the following steps:
1. Introducing into a stable cell line of the invention one or more plasmids carrying the DNA sequence coding for a full length antibody, whereby a stop codon is introduced at specific positions within the sequence
2. Purify the modified antibody with the pyrrolysine analog (nnAA) installed at desired position(s).
3. React a cytotoxin-linker derivative modified to include a functional group complimentary to the nnAA installed in the antibody with the modified antibody containing a complementary reactive group through an orthogonal chemistry
4. Purify the resulting ADC Thus, the present invention also provides ADCs whereby the antibody component has been modified to incorporate non natural amino acids bearing a unique reactive functional group at desired positions, whereby such functional group allows conjugation to a drug moiety (or protein or PEG group).

In an embodiment the present invention provides an antibody conjugate comprising an anti-Her-2 antibody which is conjugated to one or more moieties (e.g. one, two, three or four, preferably one or two, especially one) selected from protein, drug and PEG moieties via linkers comprising a triazole moiety.

In particular, the triazole moiety may be formed by reaction of an azide or alkyne moiety in the side chain of a non-natural amino acid incorporated into the sequence of the anti-Her-2 antibody and an alkyne or azide moiety attached to the protein, drug or PEG moiety.

In one embodiment, the triazole moiety is formed by reaction of an azide or alkyne moiety in the side chain of a non-natural amino acid incorporated into the sequence of the anti-Her-2 antibody and an alkyne or azide moiety attached to the protein, drug or PEG moiety under conditions of Cu(I) catalysis.

Cu(I) catalysis is accomplished by using either a native Cu(I) source such as copper iodide, copper bromide, copper chloride, copper thiolate, copper cyanide. The Cu(I) species can also be generated in situ by using a copper (II) source and a reducing agent. The copper (II) source can be copper sulfate, copper (II) chloride, or copper acetate. The reducing agent can be sodium ascorbate, dithiothreitol, TCEP, b-mercaptoethanol, hydrazine, hydroxylamine, sodium bisulfite, cystamine and cysteine.

Suitably, Cu(I) catalyzed cycloaddition are carried out in presence of ligands to stabilize the Cu(I) species present at the start of the reaction or generated in situ by reduction of a Cu(II) source such as sodium sulfate with sodium ascorbate, including TB TA, THPTA, phenanthroline derivatives, pyridylmethanimine derivatives, diethylenetriamine, bipyridine derivatives, TMEDA, N,N-bis(2-pyridylmethyl)amine (BPMA) derivatives,N,N,N',N'-tetrakis(2-pyridylmethyl) ethylenediamine (TPEN) derivatives, trialkylamines such as triethylamine, diisopropyl ethylamine, HEPES and MES.

In one embodiment a copper azide alkyne cycloaddition is used for the conjugation. Suitably, the reaction utilizes a a cytotoxic agent such as auristatin, amanitin, taxol or doxorubicin bearing a terminal alkyne. Further, the reaction employs a copper source such as copper sulfate, copper acetate, copper iodide or copper bromide; a reducing agents such as sodium ascorbate, hydrazine, hydroxylamine, sodium bisulfite, dithiothreitol, cysteine, b-mercaptoethanol; a copper chelating ligand such as Tris[(1-benzyl-1H-1,2,3-triazol-4-yl)methyl]amine (TBTA) or Tris(3-hydroxypropyltriazolylmethyl)amine (THPTA). Suitably, the reaction may be performed at 4-50° C. Suitably, the reaction time ranges from 0.5 to 48 hrs. In an alternative embodiment, a strain promoted azide alkyne cycloaddition is used for conjugation. Suitably, the reaction utilizes a dye, a PEG polymer, or cytotoxic agent such as auristatin bearing a cyclooctyne group. Suitably, the reaction is allowed to incubate at room temperature for 0.5-48 h.

Drug Moieties

Drug moieties of the present invention, such as cytotoxin drug moieties, include small molecules, natural products, synthetically derived drugs, proteins such as immunotoxins, and radionuclides.

In an embodiment, the drug moietyis an auristatin moiety eg auristatin or a derivative thereof such as monomethyl auristatin E (MMAE) (Vedotin) or monomethyl auristatin F (MMAF), Auristatin F (AF), amanitin, Paclitaxel and doxorubicin.

Other drug moieties include maytansine, paclitaxel, doxorubicin and immunotoxins such as exotoxin or bouganin as well as radionuclides such as Iodine-131, Yttrium-90, Samarium-135, and Strontium-89 which may also be incorporated into organic molecules. (see for instance: MMAE: Senter, P E, et. al, BLOOD, 102, 1458-1465. MMAF: Senter, P E, et. al., Bioconj. Chem. 2006, 17, 114-124. Maytansine: Lewis-Phillips G D, Cancer Res., 63, 9280-9290, 2008. Bouganin: MacDonald G C, et. al, J. Immunotherapy, 32 574-84, 2009.

Most suitably the drug moiety is a moiety selected from a doxorubicin, paclitaxel and auristatin moiety.

Salts

Pyrrolysine analogues described herein may optionally be employed in the form of a salt. Any such salts form an aspect of the invention. Salts of carboxylic acids may include salts formed with Group 1 and Group 2 metals, especially soluble salts such as sodium and potassium salts. Salts of amines may include salts formed with weak and strong acids, such as HCl, HBr or acetic acid.

Incorporation By Reference

All references cited herein, including patents, patent applications, papers, text books and the like, and the references cited therein, to the extent that they are not already, are hereby incorporated herein by reference in their entirety.

EXAMPLES

Example 1

Preparation of Formula V and VI Analogs

Preparation of (2S)-2-amino-6-(pent-4-enamido) hexanoic acid (Formula V.5)

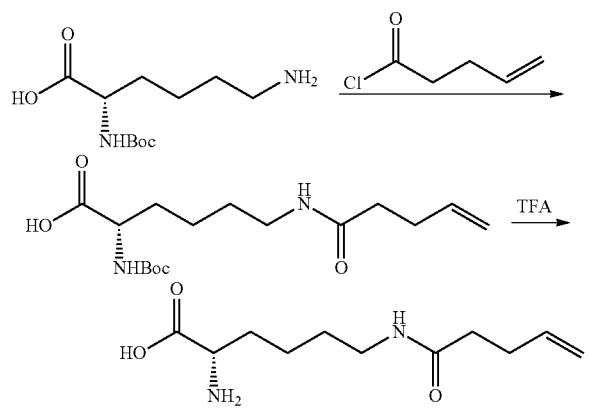

In a 25 mL roundbottomed flask was placed N-Boc-Lysine (500 mg, 2.0 mmol) suspended in dioxane (10 mL). 1M K$_2$CO$_3$ was added (5 mL) and the solution was cooled to 0 C. 4-pentenoyl chloride (224 uL, 2.0 mmol) in dioxane (2 mL) was added slowly. The solution was allowed to stir at 0 C for 1 h and then at room temperature for 4 h. The solution was transferred to a extraction funnel and partitioned between water and ether. The organic layer was removed and the aqueous layer made acidic (pH=2) with citric acid. The aqueous layer was extracted with ethyl acetate (3×50 mL), the organic layers combined and dried over sodium sulfate, filtered and concentrated. The resulting residue was carried forward into the next step.

The crude N-Boc-ε-N-4-pentenoyl amide-lysine was placed in a 50 mL round bottomed flask with acetonitrile (5 mL) and TFA (2 mL) and magnetically stirred for 2 h. The mixture was concentrated. The solution was treated with toluene (10 mL) and concentrated (2×) and acetonitrile (10 mL) and concentrated (2×). The residue was dried overnight under vacuum. The residue was taken up in MeOH and precipitated with methyl-t-butyl ether. The viscous oil was isolated by centrifugation, the supernatant was disposed. Analytical MS : m/z (ES+) expected 229.2 (M+H)+, found 230.3.

Preparation of Preparation of (S)-2-amino-6((2-oxo-2-phenylacetamide)hexanoic acid (Formula V.6)

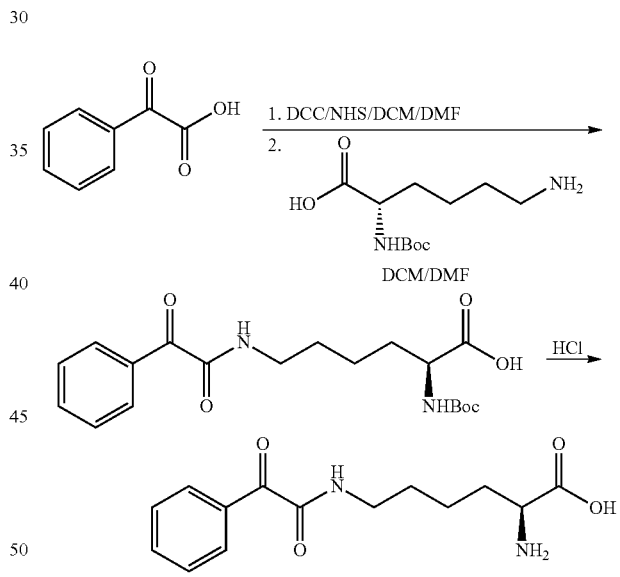

In a 50 mL round bottomed flask with magnetic stirrer was dissolved pyruvic acid (3.5 g, 23.3 mmol) in a 2:1 mixture of dichloromethane and DMF (20 mL). To this mixture was added DCC (5.7 g, 27.6 mmol) and NHS (3.2 g, 27.6 mmol). The mixture was heated to 50 C for 30 min with stirring. The solution was allowed to cool and then added through a filter to a suspension of N-Boc-Lysine (5.2 g, 21.2 mmol) in DMF (20 mL) in a separate 100 mL round bottomed flask with magnetic stirrer. Triethyl amine (8.8 mL, 63.6 mmol) was added after addition of the activated ester, and the mixture was stirred overnight. The mixture was partitioned between ethyl acetate and citric acid. The layers were separated and the aqueous layer was extracted 4 times with ethyl acetate. The organic layers were combined, dried over sodium sulfate and concentrated. The resulting residue was further purified by flash chromatography to afford the final N-Boc lysine derivative as an oil.

In a 100 mL roundbottomed flask was placed the keto-N-Boc lysine derivative (4 g, 10.6 mmol) in acetonitrile (50 mL). To this was added a solution of hydrochloric acid (15 mL, 4N in dioxane). The solution was stirred for 2 h and concentrated. Final purification by flash chromatography afforded the target amino acid. Analytical MS: m/z (ES+) expected 278.1 (M+H)+, found 279.2.

Preparation of (2S)-2-amino-6-(2-azidoacetamido)hexanoic acid (Formula V8)

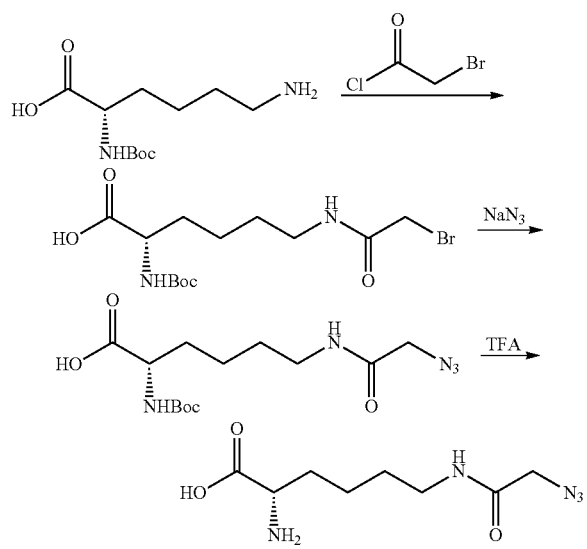

In a 25 mL roundbottomed flask was placed N-Boc-Lysine (500 mg, 2.0 mmol) suspended in dioxane (5 mL). Saturated NaHCO$_3$ was added (2 mL) and the solution was cooled to 0° C. Bromoacetyl chloride (169 uL, 2.0 mmol) in dioxane (2 mL) was added slowly. The solution was allowed to stir at 0 C for 1 h and then at room temperature for 4 h. The solution was transferred to a extraction funnel and partitioned between water and ether. The organic layer was removed and the aqueous layer made acidic (pH=2) with citric acid. The aqueous layer was extracted with ethyl acetate (3×50 mL), the organic layers combined and dried over sodium sulfate, filtered and concentrated. The resulting residue was carried forward into the next step.

In a 50 mL round bottomed flask was placed the crude N-Boc-ε-2-bromoacetyl-lysine (740 mg, 2.0 mmol) in dioxane (10 mL). To this was added a solution of sodium azide (10 mL, 1M). The solution was stirred at 60° C. overnight. The mixture was partitioned between citric acid (1M, 50 mL) and ethyl acetate (100 mL). The organic layer was retained, and the aqueous layer extracted 3 additional times. The organic layers were combined, dried over sodium sulfate and concentrated to an oil.

The crude N-Boc-ε-2-azido-acetyl-lysine was dissolved in acetonitrile (10 mL) and TFA (2 mL) was added. The mixture was stirred for 2 h and then concentrated. The solution was treated with toluene (10 mL) and concentrated (2×) and acetonitrile (10 mL) and concentrated (2×). The residue was dried overnight under vacuum. The residue was taken up in MeOH and precipitated with methyl-t-butyl ether. The viscous oil was isolated by centrifugation, the supernatant was disposed. Analytical MS: m/z (ES+) expected 229.1 (M+H)+, found 230.2.

Preparation of Hydroxy-Norleucine derivatives (Formula VI.1 and Formula VI.2)

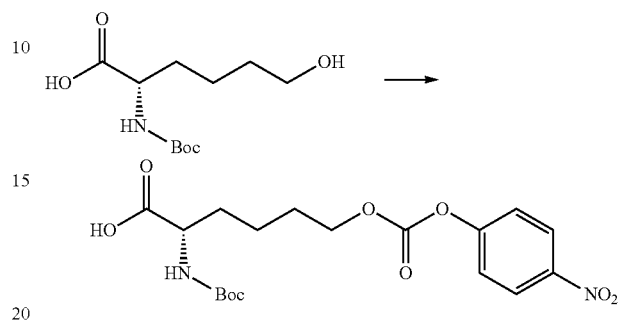

In a 100 mL roundbottomed flask with magnetic stirring was placed N-Boc-Hydroxyl Norleucine (1 g, 4.1 mmol) and acetonitrile (50 mL). The mixture was cooled to 0° C. and p-nitrophenylchloroformate (979 mg, 4.9 mmol) and Pyridine (2 mL) was added and the mixture stirred overnight. The mixture was concentrated and purified by flash chromatography. (Silica, DCM/MeOH gradient).

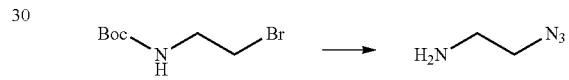

In a 100 mL roundbottomed flask with magnetic stirring was placed 2-N-Boc-ethylbromide (1 g, 4.4 mmol) in 25 mL of dioxane. To this was added a solution of sodium azide (1M, 22.2 mmol). The solution was stirred at 60 C overnight. The mixture was partitioned between water and ethyl acetate. The ethyl acetate layer was retained and the aqueous layer was extracted with ethyl acetate three additional times. The organic layers were combined, dried over sodium sulfate and concentrated to an oil.

The oil was taken up in acetonitrile (35 mL) and HCL in dioxane was added (4M, 10 mL). The mixture was stirred for two hours and concentrated under vacuum.

Preparation of (2S)-2-amino-6-{[(2-azidoethyl)carbamoyl]oxy}hexanoic acid (Formula VI.1)

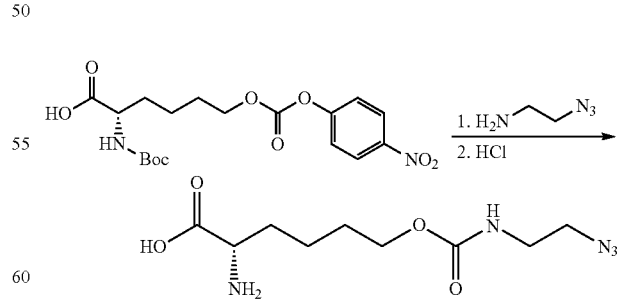

In a 50 mL round bottomed flask was placed the N-Boc-Norleucine p-nitrophenyl carbonate (503 mg, 1.2 mmoL) in dioxane (10 mL). To this was added a solution of the amino-azide (105 mg, 1.2 mmol) in dioxane (5 mL) and pyidine (1 mL). The solution was stirred overnight. The mixture was partitioned between ethyl acetate and 500 mM citric acid. The ethyl acetate layer was retained and the aqueous layer was extracted with ethyl acetate three additional times. The organic layers were combined, dried over sodium sulfate and concentrated to an oil. The oil was further purified by flash chromatography.

The isolated Boc-protected amino acid was taken up in acetontirile (15 mL) and treated with HCl in dioxane (4M, 5 mL). The mixture was stirred for two hours and concentrated under vacuum.

Alternative Preparation of (2S)-2-amino-6-[[(2-azidoethyl)carbamoyl]oxy]hexanoic acid, Formula VI.1.

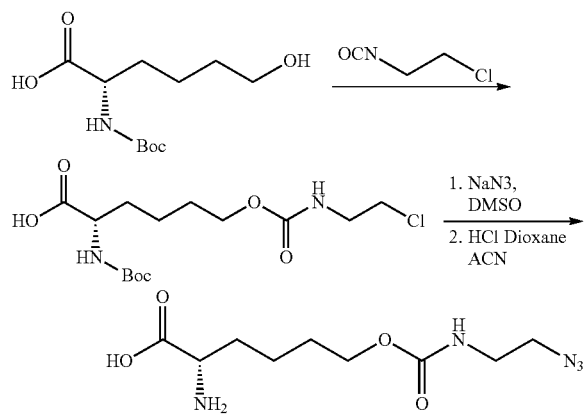

Step 1: In a 4 mL vial with magnetic stirrer was placed Boc-N-6-hydroxynorleucine (50 mg, 1 eq) and DMF (1 mL). To this was added 2-chloroethyl isocyanate (17.3 mg, 1.0 eq) and pyridine (32.3 uL, 2 eq). The vial was capped and allowed to stir for 5 h. The solution was transferred to a extraction funnel, diluted with ethylacetate and 100 mM citric acid. The mixture shaken and the layers separated. The aqueous layer was extracted with ethyl acetate two additional times. The organic layers combined, washed with 5% lithium chloride, dried with sodium sulfate, filtered and concentrated. The product was identified by mass spectrometry and taken forward into the next step directly.

Step 2: In a 4 mL vial with magnetic stirrer was placed the crude chloro derivative from above and DMSO (1 mL). Sodium azide (130 mg, 5 eq) and pyridine (32.3 uL, 2 eq) were added to the mixture and the vial was capped. The mixture was stirred overnight at 60° C. The mixture was transferred to an extraction funnel and diluted with 100 mM citric acid and ethyl acetate. The mixture was shaken and the layers separated. The aqueous layer was extracted with ethyl acetate two additional times. The organic layers combined, washed with 5% lithium chloride, dried with sodium sulfate, filtered and concentrated. The product was carried on to the next step.

Final Step: In a 20 mL vial was placed the crude Boc protected amino acid and acetonitrile (2 mL). To this was added a solution of hydrochloric acid in dioxane (4N, 2.5 mL). The solution was stirred for 2 h and then concentrated under reduced pressure. The mixture was lyophilized to a semi solid and used in translational testing. Analytical MS: m/z (ES+) expected 259.1 (M+H)+, found 260.2.

Preparation of (2S)-2-amino-6-{[(prop-2-yn-1-yl)carbamoyl]oxy}hexanoic acid (Formula VI.2)

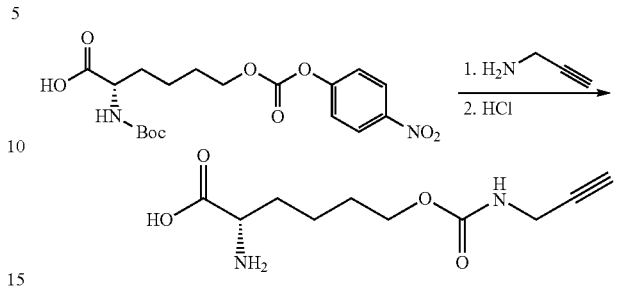

In a 50 mL round bottomed flask was placed the N-Boc-Norleucine p-nitrophenyl carbonate (337 mg, 0.8 mmoL) in dioxane (10 mL). To this was added a solution of the amino-azide (135 mg, 2.4 mmol) in dioxane (5 mL). The solution was stirred overnight. The mixture was partitioned between ethyl acetate and 500 mM citric acid. The ethyl acetate layer was retained and the aqueous layer was extracted with ethyl acetate three additional times. The organic layers were combined, dried over sodium sulfate and concentrated to an oil. The oil was further purified by flash chromatography.

The isolated Boc-protected amino acid was taken up in acetontirile (15 mL) and treated with HCl in dioxane (4M, 5 mL). The mixture was stirred for two hours and concentrated under vacuum.

Preparation of (2S)-2-amino-6-{[(prop-2-en-1-yl)carbamoyl]amino}hexanoic acid, Formula VI.3.

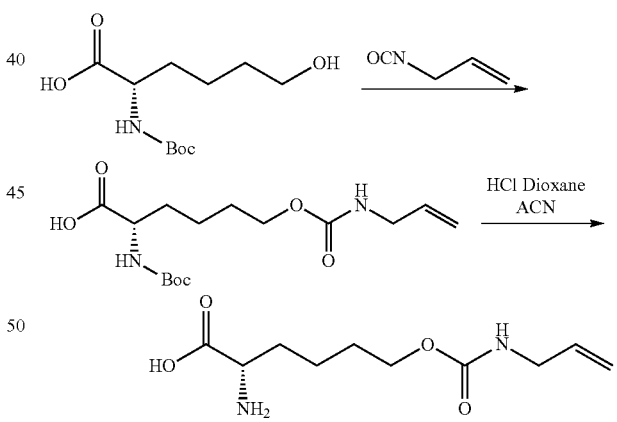

In a 4 mL vial with magnetic stirrer was placed Boc-N-6-hydroxynorleucine (50 mg, 1 eq) and DMF (1.5 mL). To this was added allyl isocyanate (18.0 uL, 1.0 eq) and pyridine (32.3 uL, 2 eq). The vial was capped and allowed to stir for 4 h. The solution was transferred to an extraction funnel, diluted with ethylacetate and 100 mM citric acid. The mixture shaken and the layers separated. The aqueous layer was extracted with ethyl acetate two additional times. The organic layers were combined, washed with 5% lithium chloride, dried with sodium sulfate, filtered and concentrated. The product was identified by mass spectrometry and taken forward into the next step directly.

In a 20 mL vial was placed the crude hydroxyl leucine—allyl carbamate derivative in acetonitrile (2 mL). To this was added a solution of hydrochloric acid in dioxane (4N, 2.5 mL). The solution was stirred for 2 h and then concentrated under reduced pressure. The mixture was lyophilized to a semi solid and used in translational testing. The product was confirmed by mass spectrometry. Additional purification could be done with ion exchange chromatography (DOWEX-50). Analytical MS: m/z (ES+) expected 230.1 (M+H)+, found 231.2.

Example 2

Translational Testing of Novel Pyrrolysine Analogs as nnAAs with a GFP Assay

An in vitro cell based assay was developed to assess the compatibility of the pylRS/tRNA pair and the the pyrrolysine analogs of the present invention (nnAAs) by and the efficiency of nnAAs integration into a target protein. For this, HEK293 cells stably expressing pylRS (3H7) were transiently transfected with plasmids for the expression of tRNApyl and a reporter construct encoding GFPY40 (containing amber codon in place of tyrosine at amino acid residue number 40 (where 1 is the initiator methionine)) using standard transfection protocols. Transfected cells were incubated with nnAAs at 2 mM for 2-3 days GFP production was analyzed qualitatively by visual inspection under the microcope. The GFP fluorescence was quantified by flow cytometry using an Accuri flow cytometer and the geometric mean of the fluorescent cells determined.

This cell based assay was used to determine whether the different nnAAs were suitable substrates for the pylRS and allowed its translation into a target protein. Cells expressing the PylRS/tRNApyl pair and containing a vector encoding the GFPY40 reporter genewere incubated in the presence of the nnAAs. nnAAs that are readily utilized by the PylRS/tRNApyl pair support the translation of the nnAA into the amber site of GFP and allow read-through of the gene producing full length GFP (fluorescent protein). The fluorescence intensity of the cells depends on the efficiency of nnAA incorporation. Thus, nnAAs that are poorly utilized produce weakly fluorescent or non-fluorescing cells. Microscopic observation identified a number of nnAAs usable by the pylRS (Table 1, Positive GFP). Furthermore, the relative expression levels in each sample was compared to those generated by substrates known to be efficiently utilized by pylRS. Formula V.1 (MFI=931,289), Formula V.2 (MFI=1,676,250) and Formula V.3 (MFI=2,250,000) (see Table 1) supported high levels of GFP expression with a geometric mean.

Analog Formulae VI.1 and VI.3 and of the present invention were found by the inventors to be incorporated in the GFP reporter gene and yield green cells under the experimental conditions used. Among these, the analog of Formula VI.1 supported high levels of GFP expression (MFI 904206) and represents an analogue that is efficiently utilized by the pylRS/tRNA pair under the experimental conditions tested (see Table 2).

TABLE 1

Formula V analog GFP results

| Formula | IUPAC Name | Positive GFP | MFI |
|---|---|---|---|
| V.1 | (2S)-2-amino-6-{[(2-azidoethoxy)carbonyl]amino}hexanoic acid | Yes | 931289 |
| V.2 | (2S)-2-amino-6-{[(prop-2-yn-1-yloxy)carbonyl]amino}hexanoic acid | Yes | 1676250 |
| V.3 | (2S)-2-amino-6-{[(prop-2-en-1-yloxy)carbonyl]amino}hexanoic acid | Yes | 2250000 |

TABLE 2

Formula VI analog GFP results

| Formula | IUPAC Name | Positive GFP Assay | MFI |
|---|---|---|---|
| VI.1 | (2S)-2-amino-6-{[(2-azidoethyl)carbamoyl]oxy}hexanoic acid | Yes | 904206 |
| VI.3 | (2S)-2-amino-6-{[(prop-2-en-1-yl)carbamoyl]oxy}hexanoic acid | Yes | |

Construction and Expression of Anti-Her2 Antibody

A full length anti-Her2 antibody containing two non natural amino acids (one in each heavy chain) (4D5-2AZ ab) was expressed in mammalian cells. A nnAA, containing an azide moiety, was incorporated at the selected sites and purified by affinity chromatography using either protein A resin (GE Healthcare) or by IgSelect (GE Healthcare, 17096901). The purified material was then concentrated and subjected to a conjugation reaction.

An antibody directed to the extracellular domain of Her2/neu was generated by cloning the variable regions of both the heavy and light chains of the mouse antibody 4D5 into vectors containing genes encoding human IgG. The variable regions of 4D5 were generated by gene synthesis using overlapping oligomers and cloned into the human IgG1 frameworks encoded by pFUSE-CHIg-hG1 (IgG1 heavy chain;gamma) and pFUSE-CHLIg-hK (light chain; kappa; Invivogen) to generate a mouse-human hybrid. Amber codons were introduced into the heavy chain (gamma) at positions K274 by site directed mutagenesis. Clones containing the amber codon were identified by DNA sequencing. To generate an integrating construct the promoters and ORF for the heavy chain was amplified by PCR and cloned by restriction enzyme digestion and ligation into pOptivec (Life Technologies). The light chain and a single copy of the tRNA were joined by two step PCR method using overlapping oligomers and cloned into available sites into the pOptivec plasmid containing the heavy chain. The construct was then transfected into a CHO cell line containing the pylRS/tRNA pair and stably transfected cell lines showing high expression of the IgG selected. This represents a second example of a cell line stably expressing a mAb containing a nnAA indicating that the process has wide applicability for the use in the expression of mAbs. This cell line was utilized to generate IgG containing the nnAAs described above. The cells were grown to a density of $1-2 \times 10^6$ cells/mL in Excel DHFR-medium (Sigma-Aldrich) and nnAA added to culture to a final concentration of 1 mM. Cells were incubated for 5 days and IgG purified from the growth medium. Supernatants were harvested and subjected to centrifugation to collect suspended cells and other debris. The supernatant was then filtered through a 0.22 um filter to remove any particulate material prior to application to a chromatography column. The filtered supernatant was applied to a 1 mL -5 mL prepacked HiTrap protein A Sepharose at 1-5 mL/min flow rate using an AKTA chromatography system. The bound material and resin were washed with PBS to remove loosely bound proteins and the bound material eluted with 100mM glycine (pH 3.0) at a flow rate of 1 mL/min. Peak fractions containing the target protein were neutralized with 0.1 fraction volumes of 1M Tris-HCl (pH8.0). All constructs were dialyzed to PBS at 4° C. for 16 hours into the final phosphate buffer. The antibody with Formula VI.1 as nnAA incorporated into both of its heavy chains at position 274 was called "4D5-2AzAb-HC274-(2S)-2-amino-6-{[(2-azidoethyl)carbamoyl]oxy}hexanoic acid".

PEGylation of 4D5-2AzAb-HC274-(2S)-2 -amino-6-{[(2-azidoethyl)carbamoyl]oxy}hexanoic acid In a 200uL PCR tube was placed phosphate buffer (5 uL, 500 mM, pH=7.4). A solution of 4D5-2AzAb-HC274-(2S)-2-amino-6-{[(2-azidoethyl)carbamoyl]oxy}hexanoic acid (Formula VI.1). (10 uL, 0.55 mg/mL) was added followed by a solution of 20 KPEG cyclooctyne (3.3, 60 mg/mL). The solution was mixed vigorously on a vortexer. The mixture was allowed to stand overnight. The mixture was diluted to 200 uL and applied to Protein-A magnetic beads. The mixture was vortexed and allowed to rotate to mix the beads for 90 min. The beads were immobilized and the run through material disposed. The beads were washed with PBS (2×) and then suspended in reducing gel buffer. Vortexed and then heated to 95 C for 3 min. The suspension was loaded directly onto an SDS-PAGE gel. Commassie staining of the SDS-PAGE gel indicated the selective PEGylation of the Heavy chain (FIG. 1, Lane 3).

Conjugation of 4D5-2AzAb-HC274-(2S)-2-amino-6-{[(2-azidoethyl)carbamoyl]oxy}hexanoic acid with Fluoroscene dye by SPAAC.

Figure 2:
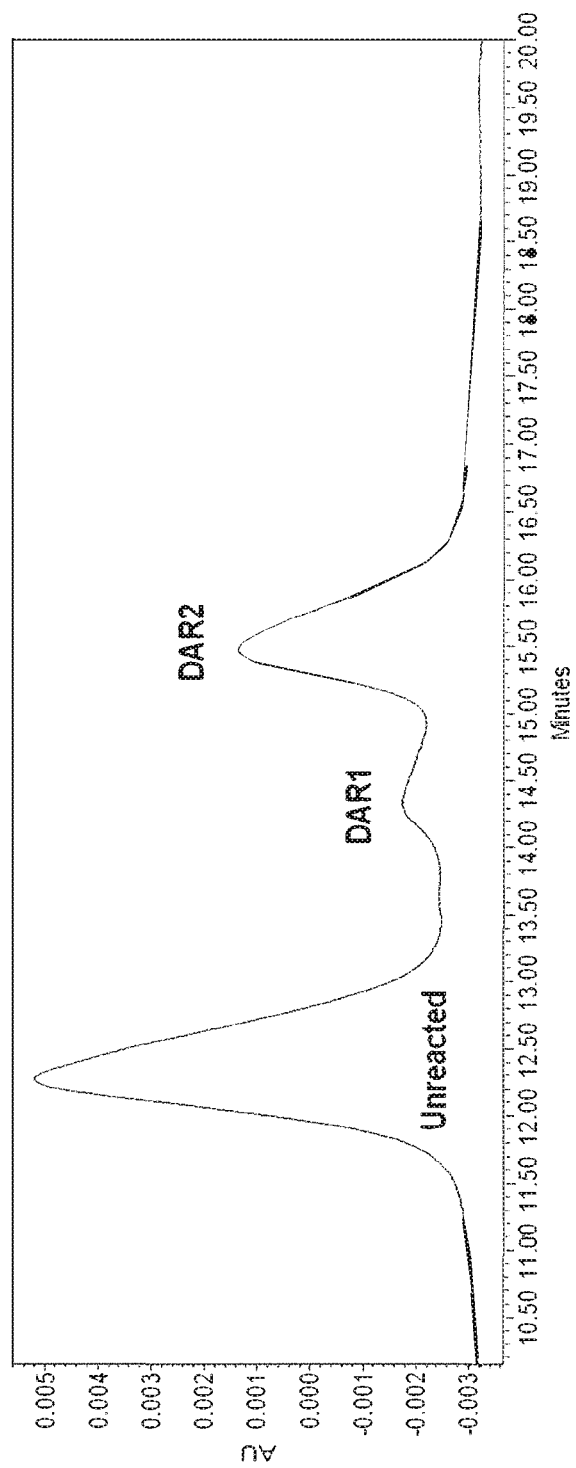
FIG. 2. HIC chromatogram of a 4D5-Auristatin F antibody drug conjugate with the antibody originally containing the pyrrolysine analog Formula VI.1, incorporated into the heavy chain.

In a 200 uL PCR tube was placed phosphate buffer (65 uL, 50 mM, pH=7.4). A solution of 4D5-2AzAb-HC274-(2S)-2-amino-6-{[(2-azidoethyl)carbamoyl]oxy}hexanoic acid (30 uL, 0.55 mg/mL) was added followed by a solution DMCO-Fluor 488 cyclooctyne (5.4, 5mM in DMSO, click chemistry tools). The solution was mixed vigorously on a vortexer. The mixture was allowed to stand for 24 h. The mixture was analyzed by HIC chromatography (Tosoh TSK-gel Butyl NPR with a gradient of 1M Sodium sulfate to phosphate buffer) showing the conjugation had occurred and resulted in a mixture wherein conjugation had occurred at one or two sites (generally referred to as DAR1 and DAR2 species; wherein DAR is defined as drug-to-antibody ratio) (FIG. 2).

```
SEQUENCE LISTING

SEQ ID NO 1
PylRS Methanosarcina mazei WT nucleotide sequence
ATGGATAAAAAACCACTAAACACTCTGATATCTGCAACCGGGCTCTGGATGTCCAGGACCGGAACAATTCATAAAATA
AAACACCACGAAGTCTCTCGAAGCAAAATCTATATTGAAATGGCATGCGGAGACCACCTTGTTGTAAACAACTCCAGG
AGCAGCAGGACTGCAAGAGCGCTCAGGCACCACAAATACAGGAAGACCTGCAAACGCTGCAGGGTTTCGGATGAGGAT
CTCAATAAGTTCCTCACAAAGGCAAACGAAGACCAGACAAGCGTAAAAGTCAAGGTCGTTTCTGCCCCTACCAGAACG
AAAAAGGCAATGCCAAAATCCGTTGCGAGAGCCCCGAAACCTCTTGAGAATACAGAAGCGGCACAGGCTCAACCTTCT
GGATCTAAATTTTCACCTGCGATACCGGTTTCCACCCAAGAGTCAGTTTCTGTCCCGGCATCTGTTTCAACATCAATA
TCAAGCATTTCTACAGGAGCAACTGCATCCGCACTGGTAAAAGGGAATACGAACCCCATTACATCCATGTCTGCCCCT
GTTCAGGCAAGTGCCCCCGCACTTACGAAGAGCCAGACTGACAGGCTTGAAGTCCTGTTAAACCCAAAAGATGAGATT
TCCCTGAATTCCGGCAAGCCTTTCAGGGAGCTTGAGTCCGAATTGCTCTCTCGCAGAAAAAAAGACCTGCAGCAGATC
TACGCGGAAGAAAGGGAGAATTATCTGGGGAAACTCGAGCGTGAAATTACCAGGTTCTTTGTGGACAGGGGTTTTCTG
GAAATAAAATCCCCGATCCTGATCCCTCTTGAGTATATCGAAAGGATGGGCATTGATAATGATACCGAACTTTCAAAA
CAGATCTTCAGGGTTGACAAGAACTTCTGCCTGAGACCCATGCTTGCTCCAAACCTTTACAACTACCTGCGCAAGCTT
GACAGGGCCCTGCCTGATCCAATAAAAATTTTTGAAATAGGCCCATGCTACAGAAAAGAGTCCGACGGCAAAGAACAC
CTCGAAGAGTTTACCATGCTGAACTTCTGCCAGATGGGATCGGGATGCACACGGGAAAATCTTGAAAGCATAATTACG
GACTTCCTGAACCACCTGGGAATTGATTTCAAGATCGTAGGCGATTCCTGCATGGTCTATGGGGATACCCTTGATGTA
ATGCACGGAGACCTGGAACTTTCCTCTGCAGTAGTCGGACCCATACCGCTTGACCGGGAATGGGGTATTGATAAACCC
TGGATAGGGGCAGGTTTCGGGCTCGAACGCCTTCTAAAGGTTAAACACGACTTTAAAAATATCAAGAGAGCTGCAAGG
TCCGAGTCTTACTATAACGGGATTTCTACCAACCTGTAA SEQ ID NO 2
PylRS, Methanosarcina mazei WT amino acid sequence
MDKKPLNTLISATGLWMSRTGTIHKIKHHEVSRSKIYIEMACGDHLVVNNSRSSRTARALRHHKYRKTCKRCRVSDED
LNKFLTKANEDQTSVKVKVVSAPTRTKKAMPKSVARAPKPLENTEAAQAQPSGSKFSPAIPVSTQESVSVPASVSTSI
SSISTGATASALVKGNTNPITSMSAPVQASAPALTKSQTDRLEVLLNPKDEISLNSGKPFRELESELLSRRKKDLQQI
YAEERENYLGKLEREITRFFVDRGFLEIKSPILIPLEYIERMGIDNDTELSKQIFRVDKNFCLRPMLAPNLYNYLRKL
DRALPDPIKIFEIGPCYRKESDGKEHLEEFTMLNFCQMGSGCTRENLESIITDFLNHLGIDFKIVGDSCMVYGDTLDV
MHGDLELSSAVVGPIPLDREWGIDKPWIGAGFGLERLLKVKHDFKNIKRAARSESYYNGISTNL SEQ ID NO 3
PylRS, Methanosarcina mazei Y384F mutant nucleotide sequence
ATGGATAAAAAACCACTAAACACTCTGATATCTGCAACCGGGCTCTGGATGTCCAGGACCGGAACAATTCATAAAATA
AAACACCACGAAGTCTCTCGAAGCAAAATCTATATTGAAATGGCATGCGGAGACCACCTTGTTGTAAACAACTCCAGG
AGCAGCAGGACTGCAAGAGCGCTCAGGCACCACAAATACAGGAAGACCTGCAAACGCTGCAGGGTTTCGGATGAGGAT
CTCAATAAGTTCCTCACAAAGGCAAACGAAGACCAGACAAGCGTAAAAGTCAAGGTCGTTTCTGCCCCTACCAGAACGA
AAAAGGCAATGCCAAAATCCGTTGCGAGAGCCCCGAAACCTCTTGAGAATACAGAAGCGGCACAGGCTCAACCTTCTG
GATCTAAATTTTCACCTGCGATACCGGTTTCCACCCAAGAGTCAGTTTCTGTCCCGGCATCTGTTTCAACATCAATAT
CAAGCATTTCTACAGGAGCAACTGCATCCGCACTGGTAAAAGGGAATACGAACCCCATTACATCCATGTCTGCCCCTG
TTCAGGCAAGTGCCCCCGCACTTACGAAGAGCCAGACTGACAGGCTTGAAGTCCTGTTAAACCCAAAAGATGAGATTT
CCCTGAATTCCGGCAAGCCTTTCAGGGAGCTTGAGTCCGAATTGCTCTCTCGCAGAAAAAAAGACCTGCAGCAGATCT
ACGCGGAAGAAAGGGAGAATTATCTGGGGAAACTCGAGCGTGAAATTACCAGGTTCTTTGTGGACAGGGGTTTTCTGG
AAATAAAATCCCCGATCCTGATCCCTCTTGAGTATATCGAAAGGATGGGCATTGATAATGATACCGAACTTTCAAAAC
AGATCTTCAGGGTTGACAAGAACTTCTGCCTGAGACCCATGCTTGCTCCAAACCTTTACAACTACCTGCGCAAGCTTG
ACAGGGCCCTGCCTGATCCAATAAAAATTTTTGAAATAGGCCCATGCTACAGAAAAGAGTCCGACGGCAAAGAACACC
```

```
TCGAAGAGTTTACCATGCTGAACTTCTGCCAGATGGGATCGGGATGCACACGGGAAAATCTTGAAAGCATAATTACGG
ACTTCCTGAACCACCTGGGAATTGATTTCAAGATCGTAGGCGATTCCTGCATGGTCTTTGGGGATACCCTTGATGTAA
TGCACGGAGACCTGGAACTTTCCTCTGCAGTAGTCGGACCCATACCGCTTGACCGGGAATGGGGTATTGATAAACCCT
GGATAGGGGCAGGTTTCGGGCTCGAACGCCTTCTAAAGGTTAAACACGACTTTAAAAATATCAAGAGAGCTGCAAGGT
CCGAGTCTTACTATAACGGGATTTCTACCAACCTGTAA

SEQ ID NO 4
PylRS, Methanosarcina mazei Y384F mutant amino acid sequence
MDKKPLNTLISATGLWMSRTGTIHKIKHHEVSRSKIYIEMACGDHLVVNNSRSSRTARALRHHKYRKTCKRCRVSDED
LNKFLTKANEDQTSVKVKVVSAPTRTKKAMPKSVARAPKPLENTEAAQAQPSGSKFSPAIPVSTQESVSVPASVSTSI
SSISTGATASALVKGNTNPITSMSAPVQASAPALTKSQTDRLEVLLNPKDEISLNSGKPFRELESELLSRRKKDLQQI
YAEERENYLGKLEREITRFFVDRGFLEIKSPILIPLEYIERMGIDNDTELSKQIFRVDKNFCLRPMLAPNLYNYLRKL
DRALPDPIKIFEIGPCYRKESDGKEHLEEFTMLNFCQMGSGCTRENLESIITDFLNHLGIDFKIVGDSCMVFGDTLDV
MHGDLELSAVVGPIPLDREWGIDKPWIGAGFGLERLLKVKHDFKNIKRAARSESYYNGISTNL SEQ ID NO 5
tRNApyl Methanosarcina mazei Go1
GGAAACCTGATCATGTAGATCGAATGGACTCTAAATCCGTTCAGCCGGGTTAGATTCCCGGGGTTTCCGCCA SEQ ID NO 6
U6 snRNA promoter
Agagggcctatttcccatgattccttcatatttgcatatacgatacaaggctgttagagagataattagaattaattt
gactgtaaacacaaagatattagtacaaaatacgtgacgtagaaagtaataatttcttgggtagtttgcagttttaaa
attatgttttaaaatggactatcatatgcttaccgtaacttgaaagtatttcgatttcttggctttatatatcttgtg
gaaaggacgaaacacc SEQ ID NO 7
U6-tRNApyl construct
Aaggtcgggcaggaagagggcctatttcccatgattccttcatatttgcatatacgatacaaggctgttagagagata
attagaattaatttgactgtaaacacaaagatattagtacaaaatacgtgacgtagaaagtaataatttcttgggtag
tttgcagttttaaaattatgttttaaaatggactatcatatgcttaccgtaacttgaaagtatttcgatttcttggc
tttatatatcttgtggaaaggacgaaacaccgaattctctagactcgagggaaacctgatcatgtagatcgaatggac
tctaaatccgttcagccgggttagattcccggggtttccggacaagtgcggttttgttt SEQ ID NO 8
GFP nuclelotide sequence
ATGGCCTCCAAAGGAGAAGAACTTTTCACTGGAGTTGTCCCAATTCTTGTTGAATTAGATGGTGATGTTAATGGGCAC
AAATTTTCTGTCAGTGGAGAGGGTGAAGGTGATGCTACATACGGAAAGCTTACCCTTAAATTTATTTGCACTACTGGA
AAACTACCTGTTCCATGGCCAACACTTGTCACTACTTTCTCTTATGGTGTTCAATGCTTTTCCCGTTATCCGGATCAT
ATGAAACGGCATGACTTTTTCAAGAGTGCCATGCCCGAAGGTTATGTACAGGAACGCACTATATCTTTCAAAGATGAC
GGGAACTACAAGACGCGTGCTGAAGTCAAGTTTGAAGGTGATACCCTTGTTAATCGTATCGAGTTAAAAGGTATTGAT
TTTAAAGAAGATGGAAACATTCTCGGACACAAACTCGAGTACAACTATAACTCACACAATGTATACATCACGGCAGAC
AAACAAAGAATGGAATCAAAGCTAACTTCAAAATTCGTCACAACATTGAAGATGGATCCGTTCAACTAGCAGACCAT
TATCAACAAAATACTCCAATTGGCGATGGCCCTGTCCTTTTACCAGACAACCATTACCTGTCGACACAATCTGCCCTT
TCGAAAGATCCCAACGAAAAGCGTGACCACATGGTCCTTCTTGAGTTTGTAACTGCTGCTGGGATTACACATGGCATG
GATCAGGCCAAGCCTTTGTCTCAAGAAGAATCCACCCTCATTGAAAGAGCAACGGCTACAATCAACAGCATCCCCATC
TCTGAAGACTACAGCGTCGCCAGCGCAGCTCTCTAGCGACGGCCGCATCTTCACTGGTGTCAATGTATATCATTTT
ACTGGGGGACCTTGTGCAGAACTCGTGGTGCTGGGCACTGCTGCTGCGGCAGCTGGCAACCTGACTTGTATCGTC
GCGATCGGAAATGAGAACAGGGCATCTTGAGCCCCTGCGGACGGTGCCGACAGGTGCTTCTCGATCTGCATCCTGGG
ATCAAAGCCATAGTGAAGGACAGTGATGGACAGCCGACGGCAGTTGGGATTCGTGAATTGCTGCCCTCTGGTTATGTG
TGGGAGGGCTAA SEQ ID NO 9
GFP amino acid sequence
MASKGEELFTGVVPILVELDGDVNGHKFSVSGEGEGDATYGKLTLKFICTTGKLPVPWPTLVTTFSYGVQCFSRYPDH
MKRHDFFKSAMPEGYVQERTISFKDDGNYKTRAEVKFEGDTLVNRIELKGIDFKEDGNILGHKLEYNYNSHNVYITAD
KQKNGIKANFKIRHNIEDGSVQLADHYQQNTPIGDGPVLLPDNHYLSTQSALSKDPNEKRDHMVLLEFVTAAGITHGM
DQAKPLSQEESTLIERATATINSIPISEDYSVASAALSSDGRIFTGVNVYHFTGGPCAELVVLGTAAAAAAGNLTCIV
AIGNENRGILSPCGRCRQVLLDLHPGIKAIVKDSDGQPTAVGIRELLPSGYVWEG SEQ ID NO 10
GFPY40 nucleotide sequence
ATGGCCTCCAAAGGAGAAGAACTTTTCACTGGAGTTGTCCCAATTCTTGTTGAATTAGATGGTGATGTTAATGGGCAC
AAATTTTCTGTCAGTGGAGAGGGTGAAGGTGATGCTACATAGGGAAAGCTTACCCTTAAATTTATTTGCACTACTGGA
AAACTACCTGTTCCATGGCCAACACTTGTCACTACTTTCTCTTATGGTGTTCAATGCTTTTCCCGTTATCCGGATCAT
ATGAAACGGCATGACTTTTTCAAGAGTGCCATGCCCGAAGGTTATGTACAGGAACGCACTATATCTTTCAAAGATGAC
GGGAACTACAAGACGCGTGCTGAAGTCAAGTTTGAAGGTGATACCCTTGTTAATCGTATCGAGTTAAAAGGTATTGAT
TTTAAAGAAGATGGAAACATTCTCGGACACAAACTCGAGTACAACTATAACTCACACAATGTATACATCACGGCAGAC
AAACAAAGAATGGAATCAAAGCTAACTTCAAAATTCGTCACAACATTGAAGATGGATCCGTTCAACTAGCAGACCAT
TATCAACAAAATACTCCAATTGGCGATGGCCCTGTCCTTTTACCAGACAACCATTACCTGTCGACACAATCTGCCCTT
TCGAAAGATCCCAACGAAAAGCGTGACCACATGGTCCTTCTTGAGTTTGTAACTGCTGCTGGGATTACACATGGCATG
GATCAGGCCAAGCCTTTGTCTCAAGAAGAATCCACCCTCATTGAAAGAGCAACGGCTACAATCAACAGCATCCCCATC
TCTGAAGACTACAGCGTCGCCAGCGCAGCTCTCTAGCGACGGCCGCATCTTCACTGGTGTCAATGTATATCATTTTAC
TGGGGGACCTTGTGCAGAACTCGTGGTGCTGGGCACTGCTGCTGCGGCAGCTGGCAACCTGACTTGTATCGTCGC
GATCGGAAATGAGAACAGGGCATCTTGAGCCCCTGCGGACGGTGCCGACAGGTGCTTCTCGATCTGCATCCTGGGAT
CAAAGCCATAGTGAAGGACAGTGATGGACAGCCGACGGCAGTTGGGATTCGTGAATTGCTGCCCTCTGGTTATGTGTG
GGAGGGCTAA
```

SEQUENCE LISTING

```
SEQ ID NO 11
GFPY40 amino acid sequence
MASKGEELFTGVVPILVELDGDVNGHKFSVSGEGEGDAT*GKLTLKFICTTGKLPVPWPTLVTTFSYGVQCFSRYPDH
MKRHDFFKSAMPEGYVQERTISFKDDGNYKTRAEVKFEGDTLVNRIELKGIDFKEDGNILGHKLEYNYNSHNVYITAD
KQKNGIKANFKIRHNIEDGSVQLADHYQQNTPIGDGPVLLPDNHYLSTQSALSKDPNEKRDHMVLLEFVTAAGITHGM
DQAKPLSQEESTLIERATATINSIPISEDYSVASAALSSDGRIFTGVNVYHFTGGPCAELVVLGTAAAAAGNLTCIV
AIGNENRGILSPCGRCRQVLLDLHPGIKAIVKDSDGQPTAVGIRELLPSGYVWEG SEQ ID NO 12
anti-Her2 (4D5) gamma nucleotide sequence
ATGGAGGCTCCCGCCCAGCTGCTCTTTCTGCTCCTTCTCTGGCTTCCCGACACAACCGGTGAGGTGCAGCTGGTGGAG
TCTGGCGGTGGCTTGGTACAGCCGGGCGGGTCCCTGCGCCTCTCCTGTGCCGCTTCCGGATTCAACATCAAAGACACG
TATATTCACTGGGTCCGTCAGGCACCTGGCAAGGGTCTGGAGTGGGTGAGCCGCATTTATCCTACCAATGGTTACACT
CGCTACGCCGACTCTGTGAAGGGCCGCTTCACCATCAGCGCCGACACGTCCAAGAACACCCTGTATCTGCAAATGAAC
AGCCTGCGTGCCGAGGACACCGCGGTGTATTACTGCAGCCGCTGGGGCGGTGATGGCTTTTACGCGATGGACTACTGG
GGCCAGGGCACCCTGGTCACCGTCTCGAGTGCTAGCACCAAGGGCCCATCGGTCTTCCCCCTGGCACCCTCCTCCAAG
AGCACCTCTGGGGGCACAGCGGCCCTGGGCTGCCTGGTCAAGGACTACTTCCCCGAACCGGTGACGGTGTCGTGGAAC
TCAGGCGCCCTGACCAGCGGCGTGCACACCTTCCCGGCTGTCCTACAGTCCTCAGGACTCTACTCCCTCAGCAGCGTG
GTGACCGTGCCCTCCAGCAGCTTGGGCACCCAGACCTACATCTGCAACGTGAATCACAAGCCCAGCAACACCAAGGTG
GACAAGAAAGTTGAGCCCAAATCTTGTGACAAAACTCACACATGCCCACCGTGCCCAGCACCTGAACCTCCTGGGGGA
CCGTCAGTCTTCCTCTTCCCCCCAAAACCCAAGGACACCCTCATGATCTCCCGGACCCCTGAGGTCACATGCGTGGTG
GTGGACGTGAGCCACGAAGACCCTGAGGTCAAGTTCAACTGGTACGTGGACGGCGTGGAGGTGCATAATGCCAAGACA
AAGCCGCGGGAGGAGCAGTACAACAGCACGTACCGTGTGGTCAGCGTCCTCACCGTCCTGCACCAGGACTGGCTGAAT
GGCAAGGAGTACAAGTGCAAGGTCTCCAACAAAGCCCTCCCAGCCCCCATCGAGAAAACCATCTCCAAAGCCAAAGGG
CAGCCCCGAGAACCACAGGTGTACACCCTGCCCCCATCCCGGGAGGAGATGACCAAGAACCAGGTCAGCCTGACCTGC
CTGGTCAAAGGCTTCTATCCCAGCGACATCGCCGTGGAGTGGGAGAGCAATGGGCAGCCGGAGAACAACTACAAGACC
ACGCCTCCCGTGCTGGACTCCGACGGCTCCTTCTTCCTCTACAGCAAGCTCACCGTGGACAAGAGCAGGTGGCAGCAG
GGGAACGTCTTCTCATGCTCCGTGATGCATGAGGCTCTGCACAACCACTACACGCAGAAGAGCCTCTCCCTGTCTCCG
GGTAAATGA SEQ ID NO 13
anti-Her2 (4D5) gamma amino acid sequence
MEAPAQLLFLLLLWLPDTTGEVQLVESGGGLVQPGGSLRLSCAASGFNIKDTYIHWVRQAPGKGLEWVSRIYPTNGYT
RYADSVKGRFTISADTSKNTLYLQMNSLRAEDTAVYYCSRWGGDGFYAMDYWGQGTLVTVSSASTKGPSVFPLAPSSK
STSGGTAALGCLVKDYFPEPVTVSWNSGALTSGVHTFPAVLQSSGLYSLSSVVTVPSSSLGTQTYICNVNHKPSNTKV
DKKVEPKSCDKTHTCPPCPAPELLGGPSVFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKAKGQPREPQVYTLPPSREEMTKNQVSLTC
LVKGFYPSDIAVEWESNGQPENNYKTTPPVLDSDGSFFLYSKLTVDKSRWQQGNVFSCSVMHEALHNHYTQKSLSLSP
GK SEQ ID NO 14
anti-Her2 (4D5) gamma_K274amber nucleotide sequence
ATGGAGGCTCCCGCCCAGCTGCTCTTTCTGCTCCTTCTCTGGCTTCCCGACACAACCGGTGAGGTGCAGCTGGTGGAG
TCTGGCGGTGGCTTGGTACAGCCGGGCGGGTCCCTGCGCCTCTCCTGTGCCGCTTCCGGATTCAACATCAAAGACACG
TATATTCACTGGGTCCGTCAGGCACCTGGCAAGGGTCTGGAGTGGGTGAGCCGCATTTATCCTACCAATGGTTACACT
CGCTACGCCGACTCTGTGAAGGGCCGCTTCACCATCAGCGCCGACACGTCCAAGAACACCCTGTATCTGCAAATGAAC
AGCCTGCGTGCCGAGGACACCGCGGTGTATTACTGCAGCCGCTGGGGCGGTGATGGCTTTTACGCGATGGACTACTGG
GGCCAGGGCACCCTGGTCACCGTCTCGAGTGCTAGCACCAAGGGCCCATCGGTCTTCCCCCTGGCACCCTCCTCCAAG
AGCACCTCTGGGGGCACAGCGGCCCTGGGCTGCCTGGTCAAGGACTACTTCCCCGAACCGGTGACGGTGTCGTGGAAC
TCAGGCGCCCTGACCAGCGGCGTGCACACCTTCCCGGCTGTCCTACAGTCCTCAGGACTCTACTCCCTCAGCAGCGTG
GTGACCGTGCCCTCCAGCAGCTTGGGCACCCAGACCTACATCTGCAACGTGAATCACAAGCCCAGCAACACCAAGGTG
GACAAGAAAGTTGAGCCCAAATCTTGTGACAAAACTCACACATGCCCACCGTGCCCAGCACCTGAACCTCCTGGGGGA
CCGTCAGTCTTCCTCTTCCCCCCAAAACCCAAGGACACCCTCATGATCTCCCGGACCCCTGAGGTCACATGCGTGGTG
GTGGACGTGAGCCACGAAGACCCTGAGGTCTAGTTCAACTGGTACGTGGACGGCGTGGAGGTGCATAATGCCAAGACA
AAGCCGCGGGAGGAGCAGTACAACAGCACGTACCGTGTGGTCAGCGTCCTCACCGTCCTGCACCAGGACTGGCTGAAT
GGCAAGGAGTACAAGTGCAAGGTCTCCAACAAAGCCCTCCCAGCCCCCATCGAGAAAACCATCTCCAAAGCCAAAGGG
CAGCCCCGAGAACCACAGGTGTACACCCTGCCCCCATCCCGGGAGGAGATGACCAAGAACCAGGTCAGCCTGACCTGC
CTGGTCAAAGGCTTCTATCCCAGCGACATCGCCGTGGAGTGGGAGAGCAATGGGCAGCCGGAGAACAACTACAAGACC
ACGCCTCCCGTGCTGGACTCCGACGGCTCCTTCTTCCTCTACAGCAAGCTCACCGTGGACAAGAGCAGGTGGCAGCAG
GGGAACGTCTTCTCATGCTCCGTGATGCATGAGGCTCTGCACAACCACTACACGCAGAAGAGCCTCTCCCTGTCTCCG
GGTAAATGA SEQ ID NO 15
anti-Her2 (4D5) gamma_K274amber amino acid sequence
MEAPAQLLFLLLLWLPDTTGEVQLVESGGGLVQPGGSLRLSCAASGFNIKDTYIHWVRQAPGKGLEWVSRIYPTNGYT
RYADSVKGRFTISADTSKNTLYLQMNSLRAEDTAVYYCSRWGGDGFYAMDYWGQGTLVTVSSASTKGPSVFPLAPSSK
STSGGTAALGCLVKDYFPEPVTVSWNSGALTSGVHTFPAVLQSSGLYSLSSVVTVPSSSLGTQTYICNVNHKPSNTKV
DKKVEPKSCDKTHTCPPCPAPELLGGPSVFLFPPKPKDTLMISRTPEVTCVVVDVSHEDPEV*FNWYVDGVEVHNAKT
KPREEQYNSTYRVVSVLTVLHQDWLNGKEYKCKVSNKALPAPIEKTISKAKGQPREPQVYTLPPSREEMTKNQVSLTC
LVKGFYPSDIAVEWESNGQPENNYKTTPPVLDSDGSFFLYSKLTVDKSRWQQGNVFSCSVMHEALHNHYTQKSLSLSP
GK SEQ ID NO 16
anti-Her2 (4D5) Kappa nucleotide sequence
ATGGAGGCTCCCGCCCAGCTGCTCTTTCTGCTCCTTCTCTGGCTTCCCGACACAACCGGTGACATCCAGATGACCCAG
TCTCCATCCTCCCTGTCTGCATCTGTGGGAGACCGTGTCACAATCACTTGCCGTGCTAGCCAGGATGTGAATACAGCG
```

SEQUENCE LISTING

```
GTGGCCTGGTATCAGCAGAAACCTGGCAAAGCCCCTAAGCTCCTGATCTATTCTGCATCCTTTTTGTACAGCGGCGTG
CCGAGCCGCTTCAGCGGCAGCCGTTCTGGTACCGATTTCACTCTCACCATCAGCTCTCTGCAACCGGAAGATTTTGCA
ACTTACTACTGTCAACAGCACTACACCACTCCTCCGACGTTCGGCCAAGGGACCAAGGTGGAAATCGAACGTACGGTG
GCTGCACCATCTGTCTTCATCTTCCCGCCATCTGATGAGCAGTTGAAATCTGGAACTGCCTCTGTTGTGCCTGCTG
AATAACTTCTATCCCAGAGAGGCCAAAGTACAGTGGAAGGTGGATAACGCCCTCCAATCGGGTAACTCCCAGGAGAGT
GTCACAGAGCAGGACAGCAAGGACAGCACCTACAGCCTCAGCAGCACCCTGACGCTGAGCAAAGCAGACTACGAGAAA
CACAAAGTCTACGCCTGCGAAGTCACCCATCAGGGCCTGAGTTCGCCCGTCACAAAGAGCTTCAACAGGGGAGAGTGT
AA

SEQ ID NO 17
anti-Her2 (4D5) Kappa amino acid sequence
MEAPAQLLFLLLLWLPDTTGDIQMTQSPSSLSASVGDRVTITCRASQDVNTAVAWYQQKPGKAPKWYSASFLYSGVPS
RFSGSRSGTDFTLTISSLQPEDFATYYCQQHYTTPPTFGQGTKVEIERTVAAPSVFIFPPSDEQLKSGTASVVCLLNN
FYPREAKVQWKVDNALQSGNSQESVTEQDSKDSTYSLSSTLTLSKADYEKHKVYACEVTHQGLSSPVTKSFNRGEC
```

REFERENCES

Fekner, T., Li, X., & Chan, M. K. (2010). Pyrrolysine Analogs for Translational Incorporation into Proteins. *European Jouranal of Organic Chemistry*, 4171-4179.

Kavran, J. M., Gundllapalli, S., O'Donoghue, P., Englert, M., Soll, D., & Steltz, T. A. (2007). Structure of pyrrolysyl-tRNA synthetase, an archaeal enzyme for genetic code innovation. *Proceedings National Academy of Sciences*, 104 (27), 11268-11273.

Kobayashi, T., Yanagisawa, T., Sakamoto, K., & Yokoyama, S. (2009). Recognition of Non-a-amino Substrates by Pyrrolysyl-tRNA Synthetase. *J. Mol. Biol.* (1352-1360), 385.

Liu, Chang C, and Peter G Schultz. "Adding New Chemistries to the Genetic Code." *Annual Review of Biochemistry*, 2010: 413-444.

Chan, Michael K, Tomasz Fekner, Xin Li, Marianne Lee, and Jennifer J Ottesen. International Patent WO2011/044255A1. 2011.

Nguyen, D. P., Lusic, H., Neumann, H. K., Deiters, A., & Chin, J. W. (2009). Genetic Encoding and Labeling of Aliphatic Azides and Alkynes in Recombinant Proteins via a Pyrrolysyl-tRNA Synthetase/tRNAcua Pair and Click Chemistry. *Journal of the American Chemical Society*, 8720-8721.

Yanagisawa, T., Ishii, R., Fukunaga, R., Kobayashi, T., Sakamoto, K., & Yokoyama, S. (2008). Crystallographic Studies on Multiple Conformational States of Active-site loops in Pyrrolysyl-tRNA synthetase. *J. Mol. Biol.*, 378, 634-652.

Yanagisawa, T., Ishii, R., Fukunaga, R., Kobayashi, T., Sakamoto, K., & Yokoyama, S. (2008). Multistep Engineering of Pyrrolysyl-tRNA Synthetase to Genetically Encode Ne-(o-Azidobenzyloxycarbonyl)lysine for Site Specific Protein Modification. *Chemistry and Biology*, 15, 1187-1197.

Yanagisawa, T., Sumida, T., Ishii, R., & Yokoyama, S. (2013). A novel crystal fom of pyrrolysyl-tRNA synthetase reveals the pre- and post-aminoacyl-tRNA synthesis conformational states of the adenylate and aminoacyl moieties and an asparagine residue in the catalytic site. *Acta Crystallographica Section D*, D69, 5-15.

All patents and patent applications referred to herein are incorporated by reference in their entirety.

The invention claimed is:

1. A pyrrolysine analog selected from the group consisting of:

(a) a pyrrolysine analog of Formula VI:

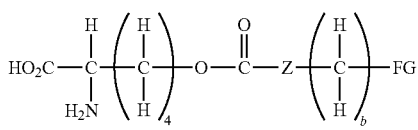

wherein
Z=$CH_2$, CH—$NH_2$, CH—OH, O, S;
FG=azide, alkene, alkyne, ketone, ester, aryl or cycloalkyne; and
b=an integer 1-4; and (b) pyrrolysine analog of Formula V:

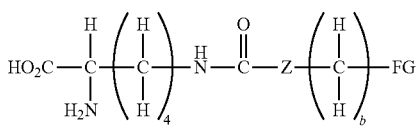

wherein
Z=bond, CH—OH, NH, or S;
b is 0 or an integer 1-7; and
FG=alkene, alkyne, aromatic ketone, ester, aryl or cycloalkyne.

2. A pyrrolysine analog of formula VI according to claim 1 wherein b is 1 or 2.

3. A pyrrolysine analog of formula VI according to claim 1 wherein FG represents —CH=CH$_2$, —C≡CH, —COR, COOCH3, phenyl substituted by halogen or cyclooctyne, wherein R=aryl.

4. A pyrrolysine analog of formula V according to claim 1 comprising:

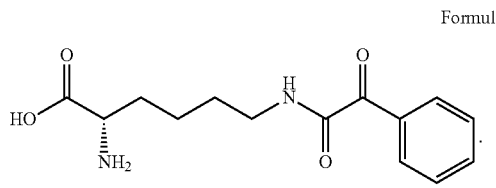

Formula V.6

5. A mutant protein containing as non-natural amino acid one or more pyrrolysine analogs according to claim 1.

6. A mutant protein according to claim 5 which is conjugated via the one or more non-natural amino acids to one or more moieties selected from proteins, cytotoxic agents, drugs and polymers.

7. A mutant protein according to claim 6 which is conjugated to a PEG moiety.

8. A mutant protein according to claim 6 which is conjugated to an antibody moiety.

9. A mutant protein according to claim 6 which is conjugated to a cytotoxic agent moiety.

10. A mutant protein according to claim 6 which is conjugated to a drug moiety.

11. A mutant protein containing as non-natural amino acid one or more pyrrolysine analogs according to claim 4.

12. A mutant protein according to claim 11 which is conjugated via the one or more non-natural amino acids to one or more moieties selected from proteins, cytotoxic agents, drugs and polymers.

13. An antibody which contains as non-natural amino acid one or more pyrrolysine analogs according to claim 1 in each heavy chain and/or light chain.

14. An antibody according to claim 13 which is conjugated via the one or more non-natural amino acids to one or more moieties selected from proteins, cytotoxic agents, drugs and polymers.

15. A pyrrolysine analog according to claim 1 having Formula VI:

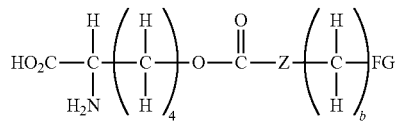

wherein
Z=CH$_2$, CH–NH$_2$, CH—OH, O, S;
FG=azide, alkene, alkyne, ketone, ester, aryl or cycloalkyne; and
b=an integer 1-4,
wherein the pyrrolysine analog is recognized by PylRS.

16. A pyrrolysine analog according to claim 1 having Formula V:

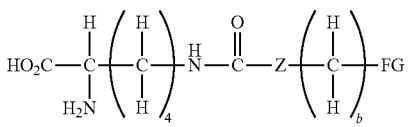

wherein
Z=bond, CH—OH, NH, or S;
b is 0 or an integer 1-7; and
FG=alkene, alkyne, aromatic ketone, ester, aryl or cycloalkyne,
wherein the pyrrolysine analog is recognized by PylRS.

* * * * *

SEQUENCE LISTING

```
<160> NUMBER OF SEQ ID NOS: 17

<210> SEQ ID NO 1
<211> LENGTH: 1365
<212> TYPE: DNA
<213> ORGANISM: Methanosarcina mazei

<400> SEQUENCE: 1
atggataaaa aaccactaaa cactctgata tctgcaaccg ggctctggat gtccaggacc      60
ggaacaattc ataaaataaa acaccacgaa gtctctcgaa gcaaaatcta tattgaaatg     120
gcatgcggag accaccttgt tgtaaacaac tccaggagca gcaggactgc aagagcgctc     180
aggcaccaca aatacaggaa gacctgcaaa cgctgcaggg tttcggatga ggatctcaat     240
aagttcctca caaaggcaaa cgaagaccag acaagcgtaa aagtcaaggt cgtttctgcc     300
cctaccagaa cgaaaaaggc aatgccaaaa tccgttgcga gagccccgaa acctcttgag     360
aatacagaag cggcacaggc tcaaccttct ggatctaaat tttcacctgc gataccggtt     420
tccacccaag agtcagtttc tgtcccggca tctgtttcaa catcaatatc aagcatttct     480
acaggagcaa ctgcatccgc actggtaaaa gggaatacga accccattac atccatgtct     540
gcccctgttc aggcaagtgc ccccgcactt acgaagagcc agactgacag gcttgaagtc     600
```

-continued

```
ctgttaaacc caaaagatga gatttccctg aattccggca agcctttcag ggagcttgag    660
tccgaattgc tctctcgcag aaaaaaagac ctgcagcaga tctacgcgga agaaagggag    720
aattatctgg ggaaactcga gcgtgaaatt accaggttct tgtggacag gggtttctg     780 gaaataaaat ccccgatcct gatccctctt gagtatatcg aaaggatggg cattgataat    840
gataccgaac tttcaaaaca gatcttcagg gttgacaaga acttctgcct gagacccatg    900
cttgctccaa acctttacaa ctacctgcgc aagcttgaca gggccctgcc tgatccaata    960 aaaattttg aaataggccc atgctacaga aaagagtccg acggcaaaga cacctcgaa    1020 gagtttacca tgctgaactt ctgccagatg ggatcgggat gcacacggga aaatcttgaa    1080
agcataatta cggacttcct gaaccacctg ggaattgatt tcaagatcgt aggcgattcc    1140
tgcatggtct atggggatac ccttgatgta atgcacggag acctggaact ttcctctgca    1200
gtagtcggac ccataccgct tgaccgggaa tggggtattg ataaaccctg gatagggca    1260 ggtttcgggc tcgaacgcct tctaaaggtt aaacacgact ttaaaaatat caagagagct    1320
gcaaggtccg agtcttacta taacgggatt tctaccaacc tgtaa                   1365
```

<210> SEQ ID NO 2
<211> LENGTH: 454
<212> TYPE: PRT
<213> ORGANISM: Methanosarcina mazei

<400> SEQUENCE: 2

```
Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
                20                  25                  30

Arg Ser Lys Ile Tyr Ile Glu Met Ala Cys Gly Asp His Leu Val Val
            35                  40                  45

Asn Asn Ser Arg Ser Ser Arg Thr Ala Arg Ala Leu Arg His His Lys
        50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240
```

Asn Tyr Leu Gly Lys Leu Glu Arg Glu Ile Thr Arg Phe Phe Val Asp
            245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
            275                 280                 285

Phe Arg Val Asp Lys Asn Phe Cys Leu Arg Pro Met Leu Ala Pro Asn
            290                 295                 300

Leu Tyr Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
            325                 330                 335

Glu His Leu Glu Glu Phe Thr Met Leu Asn Phe Cys Gln Met Gly Ser
            340                 345                 350

Gly Cys Thr Arg Glu Asn Leu Glu Ser Ile Ile Thr Asp Phe Leu Asn
            355                 360                 365

His Leu Gly Ile Asp Phe Lys Ile Val Gly Asp Ser Cys Met Val Tyr
            370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
            405                 410                 415

Trp Ile Gly Ala Gly Phe Gly Leu Glu Arg Leu Leu Lys Val Lys His
            420                 425                 430

Asp Phe Lys Asn Ile Lys Arg Ala Ala Arg Ser Glu Ser Tyr Tyr Asn
            435                 440                 445

Gly Ile Ser Thr Asn Leu
        450

<210> SEQ ID NO 3
<211> LENGTH: 1365
<212> TYPE: DNA
<213> ORGANISM: Artificial sequence
<220> FEATURE:
<223> OTHER INFORMATION: Synthetic sequence: PylRS Methanosarcina mazei
      Y384F mutant nucleotide sequence

<400> SEQUENCE: 3
atggataaaa aaccactaaa cactctgata tctgcaaccg gctctggat gtccaggacc      60 ggaacaattc ataaaataaa acaccacgaa gtctctcgaa gcaaaatcta tattgaaatg     120
gcatgcggag accaccttgt tgtaaacaac tccaggagca gcaggactgc aagagcgctc    180
aggcaccaca atacaggaa gacctgcaaa cgctgcaggg tttcggatga ggatctcaat     240
aagttcctca caaaggcaaa cgaagaccag acaagcgtaa aagtcaaggt cgtttctgcc    300
cctaccagaa cgaaaaaggc aatgccaaaa tccgttgcga gaccccgaa acctcttgag     360 aatacagaag cggcacaggc tcaaccttct ggatctaaat tttcacctgc gataccggtt    420
tccacccaag agtcagtttc tgtcccggca tctgtttcaa catcaatatc aagcatttct    480
acaggagcaa ctgcatccgc actggtaaaa gggaatacga ccccattac atccatgtct    540 gcccctgttc aggcaagtgc ccccgcactt acgaagagcc agactgacag gcttgaagtc    600
ctgttaaacc caaagatga gatttccctg aattccggca agcctttcag ggagcttgag    660
tccgaattgc tctctcgcag aaaaaaagac ctgcagcaga tctacgcgga agaaaggga g   720 aattatctgg ggaaactcga gcgtgaaatt accaggttct tgtggacag ggttttctg     780

-continued

```
gaaataaaat ccccgatcct gatccctctt gagtatatcg aaaggatggg cattgataat    840
gataccgaac tttcaaaaca gatcttcagg gttgacaaga acttctgcct gagacccatg    900
cttgctccaa acctttacaa ctacctgcgc aagcttgaca gggccctgcc tgatccaata    960
aaaatttttg aaataggccc atgctacaga aaagagtccg acggcaaaga acacctcgaa   1020
gagtttacca tgctgaactt ctgccagatg ggatcgggat gcacacggga aaatcttgaa   1080
agcataatta cggacttcct gaaccacctg gaattgatt tcaagatcgt aggcgattcc    1140
tgcatggtct ttggggatac ccttgatgta atgcacggag acctggaact ttcctctgca   1200
gtagtcggac ccataccgct tgaccgggaa tggggtattg ataaacccctg gatagggcca  1260 ggtttcgggc tcgaacgcct tctaaaggtt aaacacgact ttaaaaatat caagagagct   1320
gcaaggtccg agtcttacta taacgggatt tctaccaacc tgtaa                   1365
```

<210> SEQ ID NO 4
<211> LENGTH: 454
<212> TYPE: PRT
<213> ORGANISM: Artificial sequence
<220> FEATURE:
<223> OTHER INFORMATION: Synthetic sequence: PylRS Methanosarcina mazei
      Y384F mutant amino acid sequence

<400> SEQUENCE: 4

```
Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
                20                  25                  30

Arg Ser Lys Ile Tyr Ile Glu Met Ala Cys Gly Asp His Leu Val Val
            35                  40                  45

Asn Asn Ser Arg Ser Ser Arg Thr Ala Arg Ala Leu Arg His His Lys
        50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255
```

Arg Gly Phe Leu Glu Ile Lys Ser Pro Ile Leu Ile Pro Leu Glu Tyr
                260                 265                 270

Ile Glu Arg Met Gly Ile Asp Asn Asp Thr Glu Leu Ser Lys Gln Ile
            275                 280                 285

Phe Arg Val Asp Lys Asn Phe Cys Leu Arg Pro Met Leu Ala Pro Asn
290                 295                 300

Leu Tyr Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Cys Gln Met Gly Ser
            340                 345                 350

Gly Cys Thr Arg Glu Asn Leu Glu Ser Ile Ile Thr Asp Phe Leu Asn
        355                 360                 365

His Leu Gly Ile Asp Phe Lys Ile Val Gly Asp Ser Cys Met Val Phe
370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
            420                 425                 430

Asp Phe Lys Asn Ile Lys Arg Ala Ala Arg Ser Glu Ser Tyr Tyr Asn
        435                 440                 445

Gly Ile Ser Thr Asn Leu
    450

<210> SEQ ID NO 5
<211> LENGTH: 72
<212> TYPE: DNA
<213> ORGANISM: Methanosarcina mazei

<400> SEQUENCE: 5
ggaaacctga tcatgtagat cgaatggact ctaaatccgt tcagccgggt tagattcccg     60
gggtttccgc ca                                                        72

<210> SEQ ID NO 6
<211> LENGTH: 250
<212> TYPE: DNA
<213> ORGANISM: Artificial sequence
<220> FEATURE:
<223> OTHER INFORMATION: Synthetic sequence: U6 snRNA promoter

<400> SEQUENCE: 6
agagggccta tttcccatga ttccttcata tttgcatata cgatacaagg ctgttagaga     60
gataattaga attaatttga ctgtaaacac aaagatatta gtacaaaata cgtgacgtag    120
aaagtaataa tttcttgggt agtttgcagt tttaaaatta tgttttaaaa tggactatca    180
tatgcttacc gtaacttgaa agtatttcga tttcttggct ttatatatct tgtggaaagg    240
acgaaacacc                                                          250

<210> SEQ ID NO 7
<211> LENGTH: 372
<212> TYPE: DNA
<213> ORGANISM: Artificial sequence
<220> FEATURE:
<223> OTHER INFORMATION: Synthetic sequence: U6-tRNApyl construct

<400> SEQUENCE: 7

```
aaggtcgggc aggaagaggg cctatttccc atgattcctt catatttgca tatacgatac    60
aaggctgtta gagagataat tagaattaat ttgactgtaa acacaaagat attagtacaa   120
aatacgtgac gtagaaagta ataatttctt gggtagtttg cagttttaa aattatgttt    180
taaaatggac tatcatatgc ttaccgtaac ttgaaagtat ttcgatttct tggctttata   240
tatcttgtgg aaaggacgaa acaccgaatt ctctagactc gagggaaacc tgatcatgta   300
gatcgaatgg actctaaatc cgttcagccg ggttagattc ccggggtttc cggacaagtg   360
cggttttttgt tt                                                      372
```

<210> SEQ ID NO 8
<211> LENGTH: 1104
<212> TYPE: DNA
<213> ORGANISM: Artificial sequence
<220> FEATURE:
<223> OTHER INFORMATION: Synthetic sequence: GFP nucleotide sequence

<400> SEQUENCE: 8

```
atggcctcca aaggagaaga acttttcact ggagttgtcc caattcttgt tgaattagat    60
ggtgatgtta atgggcacaa attttctgtc agtggagagg gtgaaggtga tgctacatac   120
ggaaagctta cccttaaatt tatttgcact actggaaaac tacctgttcc atggccaaca   180
cttgtcacta ctttctctta tggtgttcaa tgcttttccc gttatccgga tcatatgaaa   240
cggcatgact ttttcaagag tgccatgccc gaaggttatg tacaggaacg cactatatct   300
ttcaaagatg acgggaacta caagacgcgt gctgaagtca agtttgaagg tgatacccct   360
gttaatcgta tcgagttaaa aggtattgat tttaaagaag atggaaacat tctcggacac   420
aaactcgagt acaactataa ctcacacaat gtatacatca cggcagacaa acaaaagaat   480
ggaatcaaag ctaacttcaa aattcgtcac aacattgaag atggatccgt tcaactagca   540
gaccattatc aacaaaatac tccaattggc gatggccctg tccttttacc agacaaccat   600
tacctgtcga cacaatctgc cctttcgaaa gatcccaacg aaaagcgtga ccacatggtc   660
cttcttgagt ttgtaactgc tgctgggatt acacatggca tggatcaggc caagcctttg   720
tctcaagaag aatccaccct cattgaaaga gcaacggcta caatcaacag catccccatc   780
tctgaagact acagcgtcgc cagcgcagct ctctctagcg acggccgcat cttcactggt   840
gtcaatgtat atcattttac tgggggacct tgtgcagaac tcgtggtgct gggcactgct   900
gctgctgcgca cagctggcaa cctgacttgt atcgtcgcga tcgaaatgaa gacaggggc    960
atcttgagcc cctgcggacg gtgccgacag gtgcttctcg atctgcatcc tgggatcaaa  1020
gccatagtga aggacagtga tggacagccg acggcagttg ggattcgtga attgctgccc  1080
tctggttatg tgtgggaggg ctaa                                         1104
```

<210> SEQ ID NO 9
<211> LENGTH: 367
<212> TYPE: PRT
<213> ORGANISM: Artificial sequence
<220> FEATURE:
<223> OTHER INFORMATION: Synthetic sequence: GFP amino acid sequence

<400> SEQUENCE: 9

```
Met Ala Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
```

```
            20                  25                  30
Glu Gly Glu Gly Asp Ala Thr Tyr Gly Lys Leu Thr Leu Lys Phe Ile
         35                  40                  45
Cys Thr Thr Gly Lys Leu Pro Val Pro Trp Pro Thr Leu Val Thr Thr
     50                  55                  60
Phe Ser Tyr Gly Val Gln Cys Phe Ser Arg Tyr Pro Asp His Met Lys
 65                  70                  75                  80
Arg His Asp Phe Phe Lys Ser Ala Met Pro Glu Gly Tyr Val Gln Glu
                 85                  90                  95
Arg Thr Ile Ser Phe Lys Asp Asp Gly Asn Tyr Lys Thr Arg Ala Glu
            100                 105                 110
Val Lys Phe Glu Gly Asp Thr Leu Val Asn Arg Ile Glu Leu Lys Gly
        115                 120                 125
Ile Asp Phe Lys Glu Asp Gly Asn Ile Leu Gly His Lys Leu Glu Tyr
    130                 135                 140
Asn Tyr Asn Ser His Asn Val Tyr Ile Thr Ala Asp Lys Gln Lys Asn
145                 150                 155                 160
Gly Ile Lys Ala Asn Phe Lys Ile Arg His Asn Ile Glu Asp Gly Ser
                165                 170                 175
Val Gln Leu Ala Asp His Tyr Gln Gln Asn Thr Pro Ile Gly Asp Gly
            180                 185                 190
Pro Val Leu Leu Pro Asp Asn His Tyr Leu Ser Thr Gln Ser Ala Leu
        195                 200                 205
Ser Lys Asp Pro Asn Glu Lys Arg Asp His Met Val Leu Leu Glu Phe
    210                 215                 220
Val Thr Ala Ala Gly Ile Thr His Gly Met Asp Gln Ala Lys Pro Leu
225                 230                 235                 240
Ser Gln Glu Glu Ser Thr Leu Ile Glu Arg Ala Thr Ala Thr Ile Asn
                245                 250                 255
Ser Ile Pro Ile Ser Glu Asp Tyr Ser Val Ala Ser Ala Ala Leu Ser
            260                 265                 270
Ser Asp Gly Arg Ile Phe Thr Gly Val Asn Val Tyr His Phe Thr Gly
        275                 280                 285
Gly Pro Cys Ala Glu Leu Val Val Leu Gly Thr Ala Ala Ala Ala Ala
    290                 295                 300
Ala Gly Asn Leu Thr Cys Ile Val Ala Ile Gly Asn Glu Asn Arg Gly
305                 310                 315                 320
Ile Leu Ser Pro Cys Gly Arg Cys Arg Gln Val Leu Leu Asp Leu His
                325                 330                 335
Pro Gly Ile Lys Ala Ile Val Lys Asp Ser Asp Gly Gln Pro Thr Ala
            340                 345                 350
Val Gly Ile Arg Glu Leu Leu Pro Ser Gly Tyr Val Trp Glu Gly
        355                 360                 365

<210> SEQ ID NO 10
<211> LENGTH: 1104
<212> TYPE: DNA
<213> ORGANISM: Artificial sequence
<220> FEATURE:
<223> OTHER INFORMATION: Synthetic sequence: GFPY40 nucleotide sequence

<400> SEQUENCE: 10
atggcctcca aaggagaaga acttttcact ggagttgtcc caattcttgt tgaattagat      60
ggtgatgtta atgggcacaa attttctgtc agtggagagg gtgaaggtga tgctacatag     120
```

```
ggaaagctta cccttaaatt tatttgcact actggaaaac tacctgttcc atggccaaca      180
cttgtcacta ctttctctta tgtgttcaa tgcttttccc gttatccgga tcatatgaaa       240
cggcatgact ttttcaagag tgccatgccc gaaggttatg tacaggaacg cactatatct     300
ttcaaagatg acgggaacta caagacgcgt gctgaagtca agtttgaagg tgatacccct     360
gttaatcgta tcgagttaaa aggtattgat tttaaagaag atggaaacat tctcggacac     420
aaactcgagt acaactataa ctcacacaat gtatacatca cggcagacaa acaaaagaat     480
ggaatcaaag ctaacttcaa aattcgtcac aacattgaag atggatccgt tcaactagca     540
gaccattatc aacaaaatac tccaattggc gatggccctg tccttttacc agacaaccat     600
tacctgtcga cacaatctgc cctttcgaaa gatcccaacg aaaagcgtga ccacatggtc     660
cttcttgagt ttgtaactgc tgctgggatt acacatggca tggatcaggc caagccttg     720 tctcaagaag aatccaccct cattgaaaga gcaacggcta caatcaacag catccccatc     780
tctgaagact acagcgtcgc cagcgcagct ctctctagcg acggccgcat cttcactggt     840
gtcaatgtat atcattttac tgggggacct tgtgcagaac tcgtggtgct gggcactgct     900
gctgctgcgg cagctggcaa cctgacttgt atcgtcgcga tcggaaatga gaacaggggc     960
atcttgagcc cctgcggacg tgtccgacag gtgcttctcg atctgcatcc tgggatcaaa     1020
gccatagtga aggacagtga tggacagccg acggcagttg ggattcgtga attgctgccc     1080
tctggttatg tgtgggaggg ctaa                                            1104
```

<210> SEQ ID NO 11
<211> LENGTH: 367
<212> TYPE: PRT
<213> ORGANISM: Artificial sequence
<220> FEATURE:
<223> OTHER INFORMATION: Synthetic sequence: GFPY40 amino acid sequence
<220> FEATURE:
<221> NAME/KEY: VARIANT
<222> LOCATION: (40)..(40)
<223> OTHER INFORMATION: Xaa is nnAA, a non natural amino acid.

<400> SEQUENCE: 11

```
Met Ala Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Xaa Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Ser Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
```

```
            165                 170                 175
Val Gln Leu Ala Asp His Tyr Gln Gln Asn Thr Pro Ile Gly Asp Gly
        180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Gln Ala Lys Pro Leu
225                 230                 235                 240

Ser Gln Glu Glu Ser Thr Leu Ile Glu Arg Ala Thr Ala Thr Ile Asn
                245                 250                 255

Ser Ile Pro Ile Ser Glu Asp Tyr Ser Val Ala Ser Ala Ala Leu Ser
            260                 265                 270

Ser Asp Gly Arg Ile Phe Thr Gly Val Asn Val Tyr His Phe Thr Gly
        275                 280                 285

Gly Pro Cys Ala Glu Leu Val Val Leu Gly Thr Ala Ala Ala Ala Ala
        290                 295                 300

Ala Gly Asn Leu Thr Cys Ile Val Ala Ile Gly Asn Glu Asn Arg Gly
305                 310                 315                 320

Ile Leu Ser Pro Cys Gly Arg Cys Arg Gln Val Leu Leu Asp Leu His
                325                 330                 335

Pro Gly Ile Lys Ala Ile Val Lys Asp Ser Asp Gly Gln Pro Thr Ala
            340                 345                 350

Val Gly Ile Arg Glu Leu Leu Pro Ser Gly Tyr Val Trp Glu Gly
        355                 360                 365

<210> SEQ ID NO 12
<211> LENGTH: 1413
<212> TYPE: DNA
<213> ORGANISM: Artificial sequence
<220> FEATURE:
<223> OTHER INFORMATION: Synthetic sequence: anti-Her2 (4D5) gamma
      nucleotide sequence

<400> SEQUENCE: 12
atggaggctc cgcccagct gctctttctg ctccttctct ggcttcccga cacaaccggt      60
gaggtgcagc tggtggagtc tggcggtggc ttggtacagc cgggcgggtc cctgcgcctc    120
tcctgtgccg cttccggatt caacatcaaa gacacgtata ttcactgggt ccgtcaggca    180
cctggcaagg gtctggagtg ggtgagccgc atttatccta ccaatggtta cactcgctac    240
gccgactctg tgaagggccg cttcaccatc agcgccgaca cgtccaagaa caccctgtat    300
ctgcaaatga acagcctgcg tgccgaggac accgcggtgt attactgcag ccgctggggc    360
ggtgatggct tttacgcgat ggactactgg ggccagggca ccctggtcac cgtctcgagt    420
gctagcacca agggcccatc ggtcttcccc ctggcaccct cctccaagag cacctctggg    480
ggcacagcgg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacccagacc    660
tacatctgca acgtgaatca caagcccagc aacaccaagg tggacaagaa agttgagccc    720
aaatcttgtg acaaaactca cacatgccca ccgtgcccag cacctgaact cctgggggga    780
ccgtcagtct tcctcttccc cccaaaaccc aaggacaccc tcatgatctc ccggacccct    840
gaggtcacat gcgtggtggt ggacgtgagc cacgaagacc ctgaggtcaa gttcaactgg    900
```

```
tacgtggacg gcgtggaggt gcataatgcc aagacaaagc cgcgggagga gcagtacaac    960
agcacgtacc gtgtggtcag cgtcctcacc gtcctgcacc aggactggct gaatggcaag   1020
gagtacaagt gcaaggtctc caacaaagcc ctcccagccc ccatcgagaa aaccatctcc   1080
aaagccaaag ggcagccccg agaaccacag gtgtacaccc tgcccccatc ccgggaggag   1140
atgaccaaga accaggtcag cctgacctgc ctggtcaaag gcttctatcc cagcgacatc   1200
gccgtggagt gggagagcaa tgggcagccg gagaacaact acaagaccac gcctcccgtg   1260
ctggactccg acggctcctt cttcctctac agcaagctca ccgtggacaa gagcaggtgg   1320
cagcagggga acgtcttctc atgctccgtg atgcatgagg ctctgcacaa ccactacacg   1380
cagaagagcc tctccctgtc tccgggtaaa tga                                1413
```

<210> SEQ ID NO 13
<211> LENGTH: 470
<212> TYPE: PRT
<213> ORGANISM: Artificial sequence
<220> FEATURE:
<223> OTHER INFORMATION: Synthetic sequence: anti-Her2 (4D5) gamma amino
acid sequence

<400> SEQUENCE: 13

```
Met Glu Ala Pro Ala Gln Leu Leu Phe Leu Leu Leu Leu Trp Leu Pro
1               5                   10                  15

Asp Thr Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Asn
        35                  40                  45

Ile Lys Asp Thr Tyr Ile His Trp Val Arg Gln Ala Pro Gly Lys Gly
    50                  55                  60

Leu Glu Trp Val Ser Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95

Asn Thr Leu Tyr Leu Gln Met Asn Ser Leu Arg Ala Glu Asp Thr Ala
            100                 105                 110

Val Tyr Tyr Cys Ser Arg Trp Gly Gly Asp Gly Phe Tyr Ala Met Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270
```

```
        Thr Leu Met Ile Ser Arg Thr Pro Glu Val Thr Cys Val Val Asp
                275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
        305                 310                 315                 320

Ser Thr Tyr Arg Val Val Ser Val Leu Thr Val Leu His Gln Asp Trp
                        325                 330                 335

Leu Asn Gly Lys Glu Tyr Lys Cys Lys Val Ser Asn Lys Ala Leu Pro
                    340                 345                 350

Ala Pro Ile Glu Lys Thr Ile Ser Lys Ala Lys Gly Gln Pro Arg Glu
                355                 360                 365

Pro Gln Val Tyr Thr Leu Pro Pro Ser Arg Glu Glu Met Thr Lys Asn
            370                 375                 380

Gln Val Ser Leu Thr Cys Leu Val Lys Gly Phe Tyr Pro Ser Asp Ile
        385                 390                 395                 400

Ala Val Glu Trp Glu Ser Asn Gly Gln Pro Glu Asn Asn Tyr Lys Thr
                        405                 410                 415

Thr Pro Pro Val Leu Asp Ser Asp Gly Ser Phe Phe Leu Tyr Ser Lys
                    420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
            450                 455                 460

Ser Leu Ser Pro Gly Lys
        465                 470

<210> SEQ ID NO 14
<211> LENGTH: 1413
<212> TYPE: DNA
<213> ORGANISM: Artificial sequence
<220> FEATURE:
<223> OTHER INFORMATION: Synthetic sequence: anti-Her2 (4D5)
      gamma_K274amber nucleotide sequence

<400> SEQUENCE: 14
atggaggctc cgcccagct gctctttctg ctccttctct ggcttcccga cacaaccggt       60
gaggtgcagc tggtggagtc tggcggtggc ttggtacagc cgggcgggtc cctgcgcctc      120
tcctgtgccg cttccggatt caacatcaaa gacacgtata ttcactgggt ccgtcaggca      180
cctggcaagg gtctggagtg ggtgagccgc atttatccta ccaatggtta cactcgctac      240
gccgactctg tgaagggccg cttcaccatc agcgccgaca cgtccaagaa caccctgtat      300
ctgcaaatga acagcctgcg tgccgaggac accgcggtgt attactgcag ccgctggggc      360
ggtgatggct tttacgcgat ggactactgg ggccagggca ccctggtcac cgtctcgagt      420
gctagcacca agggcccatc ggtcttcccc ctggcaccct cctccaagag cacctctggg      480
ggcacagcgg ccctgggctg cctggtcaag gactacttcc ccgaaccggt gacggtgtcg      540
tggaactcag gcgccctgac cagcggcgtg cacaccttcc cggctgtcct acagtcctca      600
ggactctact ccctcagcag cgtggtgacc gtgccctcca gcagcttggg cacccagacc      660
tacatctgca acgtgaatca caagcccagc aacaccaagg tggacaagaa agttgagccc      720
aaatcttgtg acaaaactca cacatgccca ccgtgcccag cacctgaact cctggggggga    780 ccgtcagtct tcctcttccc cccaaaaccc aaggacaccc tcatgatctc ccggacccct     840
```

```
gaggtcacat gcgtggtggt ggacgtgagc cacgaagacc ctgaggtcta gttcaactgg    900
tacgtggacg gcgtggaggt gcataatgcc aagacaaagc cgcggggagga gcagtacaac    960 agcacgtacc gtgtggtcag cgtcctcacc gtcctgcacc aggactggct gaatggcaag   1020
gagtacaagt gcaaggtctc caacaaagcc ctcccagccc ccatcgagaa aaccatctcc   1080
aaagccaaag ggcagccccg agaaccacag gtgtacaccc tgcccccatc ccgggaggag   1140
atgaccaaga accaggtcag cctgacctgc ctggtcaaag gcttctatcc cagcgacatc   1200
gccgtggagt gggagagcaa tgggcagccg gagaacaact acaagaccac gcctcccgtg   1260
ctggactccg acggctcctt cttcctctac agcaagctca ccgtggacaa gagcaggtgg   1320
cagcagggga acgtcttctc atgctccgtg atgcatgagg ctctgcacaa ccactacacg   1380
cagaagagcc tctccctgtc tccgggtaaa tga                                1413
```

<210> SEQ ID NO 15
<211> LENGTH: 470
<212> TYPE: PRT
<213> ORGANISM: Artificial sequence
<220> FEATURE:
<223> OTHER INFORMATION: Synthetic sequence: anti-Her2 (4D5)
     gamma_K274amber amino acid sequence
<220> FEATURE:
<221> NAME/KEY: VARIANT
<222> LOCATION: (297)..(297)
<223> OTHER INFORMATION: Xaa is nnAA, a non natural amino acid.

<400> SEQUENCE: 15

```
Met Glu Ala Pro Ala Gln Leu Leu Phe Leu Leu Leu Leu Trp Leu Pro
1               5                   10                  15

Asp Thr Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Asn
        35                  40                  45

Ile Lys Asp Thr Tyr Ile His Trp Val Arg Gln Ala Pro Gly Lys Gly
    50                  55                  60

Leu Glu Trp Val Ser Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95

Asn Thr Leu Tyr Leu Gln Met Asn Ser Leu Arg Ala Glu Asp Thr Ala
            100                 105                 110

Val Tyr Tyr Cys Ser Arg Trp Gly Gly Asp Gly Phe Tyr Ala Met Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240
```

```
Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Xaa Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 16
<211> LENGTH: 705
<212> TYPE: DNA
<213> ORGANISM: Artificial sequence
<220> FEATURE:
<223> OTHER INFORMATION: Synthetic sequence: anti-Her2 (4D5) Kappa
      nucleotide sequence

<400> SEQUENCE: 16
atggaggctc cgcccagct gctctttctg ctccttctct ggcttcccga cacaaccggt      60
gacatccaga tgacccagtc tccatcctcc ctgtctgcat ctgtgggaga ccgtgtcaca     120
atcacttgcc gtgctagcca ggatgtgaat acagcggtgg cctggtatca gcagaaacct    180
ggcaaagccc ctaagctcct gatctattct gcatcctttt tgtacagcgg cgtgccgagc    240
cgcttcagcg gcagccgttc tggtaccgat ttcactctca ccatcagctc tctgcaaccg    300
gaagattttg caacttacta ctgtcaacag cactacacca ctcctccgac gttcggccaa    360
gggaccaagg tggaaatcga acgtacggtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
```

```
ctgagttcgc ccgtcacaaa gagcttcaac aggggagagt gttaa          705
```

<210> SEQ ID NO 17
<211> LENGTH: 234
<212> TYPE: PRT
<213> ORGANISM: Artificial sequence
<220> FEATURE:
<223> OTHER INFORMATION: Synthetic sequence: anti-Her2 (4D5) Kappa amino
      acid sequence

<400> SEQUENCE: 17

```
Met Glu Ala Pro Ala Gln Leu Leu Phe Leu Leu Leu Trp Leu Pro
1               5                   10                  15

Asp Thr Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Tyr
            100                 105                 110

Thr Thr Pro Pro Thr Phe Gly Gln Gly Thr Lys Val Glu Ile Glu Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```